US008778360B2

(12) United States Patent
Suckow et al.

(10) Patent No.: US 8,778,360 B2
(45) Date of Patent: Jul. 15, 2014

(54) EXTRACELLULAR MATRIX CANCER VACCINE ADJUVANT

(75) Inventors: Mark A. Suckow, Granger, IN (US); William R. Wolter, South Bend, IN (US)

(73) Assignee: University of Notre Dame, Notre Dame, IN (US)

(*) Notice: Subject to any disclaimer, the term of this patent is extended or adjusted under 35 U.S.C. 154(b) by 0 days.

(21) Appl. No.: 11/583,771

(22) Filed: Oct. 20, 2006

(65) Prior Publication Data

US 2010/0233214 A1  Sep. 16, 2010

Related U.S. Application Data

(60) Provisional application No. 60/730,379, filed on Oct. 27, 2005.

(51) Int. Cl.
*A61K 9/00* (2006.01)
*A61K 9/14* (2006.01)
*A61K 9/70* (2006.01)

(52) U.S. Cl.
USPC ........ 424/277.1; 424/423; 424/443; 424/484; 424/489

(58) Field of Classification Search
None
See application file for complete search history.

(56) References Cited

U.S. PATENT DOCUMENTS

| | | | |
|---|---|---|---|
| 2,172,903 A | 9/1939 | Charping | |
| 3,346,401 A | 10/1967 | Kumarbarat | |
| 3,562,820 A | 2/1971 | Braun | |
| 3,810,473 A | 5/1974 | Cruz, Jr. et al. | |
| 4,502,159 A | 3/1985 | Woodroof et al. | |
| 4,578,067 A | 3/1986 | Cruz, Jr. | |
| 4,902,508 A | 2/1990 | Badylak et al. | |
| 4,956,178 A | 9/1990 | Badylak et al. | |
| 5,028,695 A | 7/1991 | Eckmayer et al. | |
| 5,275,826 A | 1/1994 | Badylak et al. | |
| 5,281,422 A | 1/1994 | Badylak et al. | |
| 5,336,616 A | 8/1994 | Livesey et al. | |
| 5,352,463 A | 10/1994 | Badylak et al. | |
| 5,372,821 A | 12/1994 | Badylak et al. | |
| 5,437,287 A | 8/1995 | Phillips et al. | |
| 5,460,962 A | 10/1995 | Kemp | |
| 5,480,424 A | 1/1996 | Cox | |
| 5,507,810 A | 4/1996 | Prewett et al. | |
| 5,554,389 A | 9/1996 | Badylak et al. | |
| 5,695,998 A * | 12/1997 | Badylak et al. ............... | 435/391 |
| 5,733,337 A | 3/1998 | Carr, Jr. et al. | |
| 5,782,914 A | 7/1998 | Schankereli | |
| 5,837,269 A | 11/1998 | Daynes et al. | |
| 6,120,991 A | 9/2000 | Carter et al. | |
| 6,156,305 A * | 12/2000 | Brauker et al. ............ | 424/93.21 |
| 6,206,931 B1 | 3/2001 | Cook et al. | |
| 6,207,147 B1 * | 3/2001 | Hiserodt et al. ............. | 424/93.1 |
| 6,218,166 B1 * | 4/2001 | Ravindranath et al. ....... | 435/366 |
| 6,264,992 B1 | 7/2001 | Voytik-Harbin et al. | |
| 6,277,368 B1 | 8/2001 | Hiserodt et al. | |
| 6,403,104 B1 * | 6/2002 | Berd ........................... | 424/277.1 |
| 6,406,689 B1 | 6/2002 | Falkenberg et al. | |
| 6,451,971 B1 * | 9/2002 | Akiyama et al. ............... | 530/326 |
| 6,548,066 B1 | 4/2003 | Michaeli et al. | |
| 6,699,483 B1 * | 3/2004 | Dalgleish et al. .......... | 424/277.1 |
| 7,015,205 B1 | 3/2006 | Wallack et al. | |
| 7,090,853 B2 | 8/2006 | Kapp et al. | |
| 7,175,652 B2 | 2/2007 | Cook et al. | |
| 7,550,004 B2 | 6/2009 | Bahler et al. | |
| 2001/0006631 A1 | 7/2001 | Hiserodt et al. | |
| 2002/0001595 A1 | 1/2002 | Sonntag et al. | |
| 2003/0014126 A1 | 1/2003 | Patel et al. | |
| 2004/0013712 A1 | 1/2004 | Parma | |
| 2006/0099675 A1 | 5/2006 | Benard | |
| 2006/0147433 A1 | 7/2006 | Hiles | |
| 2006/0265053 A1 | 11/2006 | Hunt | |
| 2007/0035843 A1 | 2/2007 | Cassarly | |
| 2007/0128174 A1 | 6/2007 | Kleinsek et al. | |
| 2008/0107665 A1 | 5/2008 | Suckow et al. | |
| 2008/0160049 A1 | 7/2008 | Suckow et al. | |
| 2008/0260800 A1 | 10/2008 | Suckow et al. | |
| 2009/0220461 A1 | 9/2009 | Suckow et al. | |
| 2009/0248144 A1 | 10/2009 | Bahler et al. | |

(Continued)

FOREIGN PATENT DOCUMENTS

AU  2007309193 A1  5/2008
AU  2007345673 A1  8/2008

(Continued)

OTHER PUBLICATIONS

Evans et al., Q. J. Med 1999: 92: 299-307.*
Finn et al., Curr. Opin. Immunol., 2002, 14: 172-177.*
Komenaka et al., Clinics in Dermatology, 2004, 22: 251-265.*
Wilson et al., Anatomical Record, 1997, 249: 63-73.*
Sanderson, Nature, 1974, 248:690-691.*
Wheeler (Salud p'ublica de M'exico, 1997, vol. 39, pp. 283-287).*
Efferson et al (Anticancer research, 2005, vol. 25, pp. 715-724).*
Bachman et al (Journal of Immunology, 2005, vol. 175, pp. 4677-4685).*
Chou et al (Cancer Research, 1989, vol. 49, pp. 5371-5376).*
Suckow et al (Cancer Immunology Immunopharmacology, vol. 54, pp. 571-576, published on-line Feb. 1, 2005).*
Donald et al (Invasion and Metastasis, 1998-1999, vol. 18, pp. 165-175).*

(Continued)

*Primary Examiner* — Karen Canella
(74) *Attorney, Agent, or Firm* — Husch Blackwell LLP; Denise L. Mayfield

(57) ABSTRACT

Compositions suitable for use as adjuvants in the preparation of vaccines, particularly those vaccines useful in the treatment of cancer, are provided. Methods for inhibiting tumor growth in an animal are also disclosed. Methods for immunizing an animal against cancer, such as prostate cancer, are also described. The adjuvants described are comprised of an extracellular matrix material, such as small intestinal submucosal (SIS) tissue. The preparations may take the form of sheets, gels, liquids (injectable), trocar or other solid or semi-solid preparation. The invention provides for enhanced tumor inhibition of 2-fold or greater, compared to vaccine preparations without the extracellular matrix material, or from 4- to 5-fold, compared to preparations without the adjuvant promoting extracellular materials.

19 Claims, 7 Drawing Sheets

(56) References Cited

U.S. PATENT DOCUMENTS

| | | |
|---|---|---|
| 2010/0136050 A1 | 6/2010 | Suckow et al. |
| 2010/0233214 A1 | 9/2010 | Suckow et al. |
| 2011/0076305 A1 | 3/2011 | Suckow et al. |
| 2011/0135690 A1 | 6/2011 | Suckow |
| 2011/0150934 A1 | 6/2011 | Suckow |

FOREIGN PATENT DOCUMENTS

| | | | |
|---|---|---|---|
| CA | 2667075 A1 | | 5/2008 |
| CA | 2627364 A1 | | 7/2008 |
| CN | 101730541 A | | 6/2010 |
| EP | 2109667 A2 | | 10/2009 |
| EP | 2114444 A1 | | 11/2009 |
| JP | 2010507584 A | | 3/2010 |
| JP | 516763 | | 5/2010 |
| WO | 9624661 | | 8/1996 |
| WO | WO 9736495 A1 | * | 10/1997 |
| WO | WO00/09140 | * | 2/2000 |
| WO | 03/017745 A2 | | 3/2003 |
| WO | WO 03100034 A2 | * | 12/2003 |
| WO | WO2006/095330 | * | 9/2006 |
| WO | 2007/035363 A2 | | 3/2007 |
| WO | 2007/035843 A2 | | 3/2007 |
| WO | WO2008/051852 | | 5/2008 |
| WO | WO2008/094276 | | 8/2008 |
| WO | WO2008/112344 | | 9/2008 |
| WO | WO2009/108656 | | 9/2009 |

OTHER PUBLICATIONS

Edwards B.K., et al., *J Natl Cancer Inst* (2005); 97(19):1407-27.
Greenlee RT, Harmon M.B., Murray T, Thun M., "Cancer Statistics", (2001), *CA Cancer J Clin.*, (2001);51:15-36.
Simons J.W., Sacks N., *Urol. Oncol.*, (2006);24:419-424.
Fukino K, et al., *Cancer Res.*, (2004);64(20):7231-6.
Bissell MJ, et al., *J. Cell Sci. Suppl.*, (1987);8(3):327-43.
Matrisian LM, et al., *Cancer Res.*, (2001);61(9):3844-6.
Shekhar MP, et al., *Cancer Res.*, (2001);61(4):1320-6.
Tatenhorst L, et al. "Genes Associated with Fast Glioma Cell Migration in vitro and in vivo", *Brain Pathol.*, (2005);15(1):46-54.
Moschella F, et al., *Oncol Res.*, (2003);14(3):133-45.
Brewer J.M., "How do Aluminum Adjuvants Work?" *Immunol Lett.*, (2006); 102(1):10-5.
Lindblad, EB., *Immunol Cell Biol.*, (2004);82(5):497-505.
Barr, TA, et. al., Vaccine, (2006); 24(17):3399-407.
Hodge, J.W., *Front Biosci.*, (2006); 11:788-803.
Knoll L.D., *Urology*, (2001);57:753-757.
Knoll L.D., *Urology*, (2002);59:758-761.
Mantovani F, et al., *Eur Urol.*, (2003);44:600-602.
O'Connor RC, Patel RV, Steinberg GD., *J Urology*, (2001);165:1995.
O'Connor RC, Hollowell CM, Steinberg GD., *Urology*, (2002);60:697x-697xii.
O'Connor RC, Harding JN, Steinberg GD., *Urology*. (2002);60:906-909.
Paradiso M, et. al., *Arch Ital Urol. Andro.*, (2003);75:116-118.
Weiser AC, et al., *J. Urol*, (2003);170:1593-1595.
Oasis, Benbow M., "An Innovative Alternative Dressing for Chronic Wounds", *Br. J. Nurs.*, (2001);10:1489-1492.
Brown-Etris M, Cutshall WD, Hiles M.C., *Wounds*, (2002);14:150-166.
Schultz DJ, et al., *J. Am. Coll. Surg.*, (2002); 194:541-543.
Suckow M.A., et al., *Journal of Investigative Surgery*, (1999); 12:277-287.
Badylak, S.F., *Small Intestinal Submucosa (SIS): A Biomaterial Conducive to Smart Tissue Remodeling, Tissue Engineering: Current Perspectives*, Bell E (ed). Burkhauser.
Badylak, S.F., "The Extracellular Matrix as a Scaffold for Tissue Reconstruction", *Seminars in Cellular and Developmental Biology*, (2002); 13:377-383.
Suckow MA, Hodde JP, Wolters WR, Hiles MC., *J. Wound Care*, (2005), 14:137-140.
Suckow MA, Hodde JP, Wolter WR, Hiles MC., "Surgical Repair of Experimental Achilles Tenotomy with Porcine Renal Capsule Material in a Rat Model" *J. Mater Sci. Mater. Med.*
Lantz, G.C., et al., *J. Invest. Surg.*, (1993), 6:297.
Badylak, S.F., Lantz, G., Coffey, A., and Geddes, L.A., *J. Surg. Res.*, (1989), 47:74.
Lantz, G.C., Badylak, S.F., Coffey, A.C., Geddes, L.A., Blevins, W.E., *J. Invest. Surg.*, (1990), 3:217.
Hodde, J.P., and Hiles, M.C., *Biotechnol. Bioeng.*,(2002), 79:211.
Pollard M, Suckow M.A., "Hormone-Refractory Prostate Cancer in the Lobund-Wistar Rat", *Experimental Biology and Medicine*, (2005), 230:520-526.
Suckow MA, Wolter WR, Pollard M., *Cancer Immunology and Immunotherapy*, (2005); 54:571-576.
Pollard M, Luckert P.H., *J. Natl. Cancer Inst.*, (1975); 54:643-49.
Badylak SF, Record R, Lindberg K, Hodde J, Park K., *Journal of Biomaterials Sciences Polymer Edition*, (1998); 9:863-878.
Hodde, JP., et al., *J. Surg. Res.*, (2004); 120: 189-194.
Culora GA, Ramsay AD, Theaker JM., *J. Clin. Pathol.*, (1996); 49:844-847.
McDevitt CA, Wildey GM, Cutrone RM., *J. Biomed. Mater. Res.*, (2003);67A:637-646.
Bello-DeOcampo D, Tindall D.J., "TGF-beta/Smad signaling in Prostate Cancer", *Curr. Drug Targets*, (2003);4:197-210.
Voytik-Harbin S.L., et al., *Tissue Eng.*, (1998);4:157-174.
Michael A., et al., *Clin, Cancer Res.* (2005); 11:4469-4478.
Pilla L, et al., *Cancer Immunol Immunother.*, (2006);55:958-968.
Berd D, et al., *J. Clin Oncol.*, (1997);15:2359-2370.
Petrovsky N., *Vaccine*, (2006);24 Suppl. 2:S2-26-9.
Bendandi, M. et al., *Leuk. Lymphoma.*, (2006);47:29-37.
Redfern C.H., et al al. *J Clin Oncol.*, (2006);24:3107-12.
Totterman TH, Loskog A, Essand M., *BJU Int.*, (2005);96:728-735.
Mosolits S, Nilsson B, Mellstedt H., "Towards Therapeutic Vaccines for Colorectal Carcinoma: A Review of Clinical Trials" *Expert Rev. Vaccines*, (2005);4:329-350.
He X, Tsang TC, Zhang T, Luo P, Harris DT., *Vaccine*, (2004);23:1966-1972.
Wei Y, Sticca R.P., et al., *Int. J. Oncol.*, (2006);28:585-593.
Rousseau RF, et al., *Blood*, (2006);107:1332-1341.
Akhurst, Rosemary, *J. Clin. Invest.* (2002); 1533-1536.
Kenney RT, et al., *J. Infect. Dis.*, (2004);190:774-782.
Skountzou I, et al., *Vaccine*, (2006);24:6110-6119.
Glenn GM, Kenney R.T., *Curr. Topics Microbiol. Immunol.*, (2006);304:247-268.
Rechsteiner G, et al., *J. Immunol.*, (2005);174:2476-2480.
Huang C.M, et al., *Proteomics*, (2005);5:1013-1023.
Michael, et al., *Clin. Cancer Res.*, (2005);11:4469-4478.
Gu, Y., and Dai, K., Zhonghua Yi Xue Za Zhi. National Medical Journal of China, (2002);vol. 82, No. 18:1279-1282.
Hodde, et al. Small Intestinal Submucosa Does Not Promote PAIII Tumor Growth in Lobund-Wistar Rats, 2004, vol. 120, pp. 189-194, especially p. 190, $2^{nd}$ column.
Wilson, et al. Human Prostate Tumor Angiogenesis in Nude Mice: Metalloprotease and Plasminogen Activator Activities During Tumor Growth and Neovascularization of Subcutaneously Injected Matrigel Impregnated With Human Prostate Tumor Cells, Anatomical Record, 1997, 249:63-73, especially p. 63.
Abraham, et al. (2000) J. Biomed. Mater Res., 29:442-452.
Higaki, et al. (2004) Vaccine, 19:3091-3096.
Hodde, et al. (2004) J. Surg. Res., 120:189-194.
International Search Report and Written Opinion, International Application PCT/US08/51877 mailed Sep. 17, 2008.
Aguzzi et al., (2003), "Immune system and peripheral nerves in propagation of prions to CNS," *Br Med Bull.*, 2003;66:141-59.
Allman et al., (2001), "Xenogeneic extracellular matrix grafts elicit a TH2-restricted immune response," *Transplantation*, 71:1631-1640.
Arbel et al., (2003), "Generation of antibodies against prion protein in wild-type mice via helix 1 peptide immunization," *J Neuroimmunol.*, 144(1-2):38-45.
Banzhoff et al., (2003), "A new MF59-adjuvanted influenza vaccine enhances the immune response in the elderly with chronic diseases: results from an immunogenicity meta-analysis," *Gerontology*, 49(3):177-84.

(56) References Cited

OTHER PUBLICATIONS

Brando et al., (2007), "Murine immune responses to liver-stage antigen 1 protein FMP011, a malaria vaccine candidate, delivered with adjuvant AS01B or AS02A," *Infect Immun.*, 75(2):838-45.

Caglar et al., (2005), "Effect of monophosphoryl lipid A on antibody response to diphtheria toxin and its subunits," *APMIS*, 113(4):256-63.

de Souza Matos et al., (2000), "Immunostimulatory effects of polar glycopeptidolipids of Mycobacterium chelonae for inactivated rabies vaccine," *Vaccine*, 18(20):2125-31.

Desai et al., (2000), "Immune response with biodegradable nanospheres and alum: studies in rabbits using staphylococcal enterotoxin B-toxoid," *J Microencapsul.*, 17(2):215-25.

Eldridge et al., (1991), "Biodegradable and biocompatible poly(DL-lactide-co-glycolide) microspheres as an adjuvant for staphylococcal enterotoxin B toxoid which enhances the level of toxin-neutralizing antibodies," *Infect Immun.*, 59(9):2978-86.

Enari et al., (2001), "Scrapie prion protein accumulation by scrapie-infected neuroblastoma cells abrogated by exposure to a prion protein antibody," *Proc Natl Acad Sci U S A*, 98(16):9295-9.

Flick-Smith et al., (2002), "Mucosal or parenteral administration of microsphere-associated *Bacillus anthracis* protective antigen protects against anthrax infection in mice," *Infect Immun.*, 70(4):2022-8.

Gilch et al., (2003), "Polyclonal anti-PrP auto-antibodies induced with dimeric PrP interfere efficiently with PrPSc propagation in prion-infected cells," *J Biol Chem.*, 278(20):18524-31.
Griffiths et al., (1997), "Liposomally-encapsulated ricin toxoid vaccine delivered intratracheally elicits a good immune response and protects against a lethal pulmonary dose of ricin toxin," *Vaccine*, 15(17-18):1933-9.
Hanan et al., (2001), "Antiaggregating antibody raised against human PrP 106-126 recognizes pathological and normal isoforms of the whole prion protein," *Cell Mol Neurobiol.*, 21(6):693-703.
Hanan et al., (2001), "Immunomodulation of the human prion peptide 106-126 aggregation," Biochem Biophys Res Commun., 280(1):115-20.
Hedlund et al., (2001), "Negligible adjuvant effect for antibody responses and frequent adverse events associated with IL-12 treatment in humans vaccinated with pneumococcal polysaccharide," *Vaccine*, 20(1-2):164-9.
Higgins et al., (1996), "MF59 adjuvant enhances the immunogenicity of influenza vaccine in both young and old mice," *Vaccine*, 14(6):478-84.
Jaganathan et al., (2006), "Strong systemic and mucosal immune responses to surface-modified PLGA microspheres containing recombinant hepatitis B antigen administered intranasally," *Vaccine*, 24(19):4201-11.
Kende et al., (2006), "Enhancement of intranasal vaccination in mice with deglycosylated chain A ricin by LTR72, a novel mucosal adjuvant," *Vaccine*, 15;24(12):2213-21.
Kenney et al., (1999), "Protective immunity using recombinant human IL-12 and alum as adjuvants in a primate model of cutaneous leishmaniasis," J Immunol., 163(8):4481-8.
Koller et al., (2002), "Induction of antibodies against murine full-length prion protein in wild-type mice," *J Neuroimmunol.*, 132(1-2):113-6.
Langermans et al., (2005), "Effect of adjuvant on reactogenicity and long-term immunogenicity of the malaria Vaccine ICC-1132 in macaques," *Vaccine*, 23(41):4935-43.
Levesque et al., (2006), "Association between immunogenicity and adsorption of a recombinant *Streptococcus pneumoniae* vaccine antigen by an aluminum adjuvant," *Hum Vaccin.*, 2(2):74-7.
Martin, (1997), "Development of an adjuvant to enhance the immune response to influenza vaccine in the elderly," *Biologicals*, 25(2):209-131.
Mendez et al., (2003), "Coinjection with CpG-containing immunostimulatory oligodeoxynucleotides reduces the pathogenicity of a live vaccine against cutaneous Leishmaniasis but maintains its potency and durability," *Infect Immun.* 71(9):5121-9.
Mullen et al., (2006), "Enhancement of functional antibody responses to AMA1-C1/Alhydrogel, a *Plasmodium falciparum* malaria vaccine, with CpG oligodeoxynucleotide," *Vaccine*, 24(14):2497-505.
Palese, (2006), "Making better influenza virus vaccines?" *Emerg Infect Dis.*, 12(1):61-5.
Peng et al., (2006), "Novel vaccines for the treatment of chronic HBV infection based on mycobacterial heat shock protein 70," Vaccin, 24(7):887-96.
Peretz et al., (2001), "Antibodies inhibit prion propagation and clear cell cultures of prion infectivity," *Nature*, 412(6848):739-43.
Petrik et al., (2007), "Aluminum adjuvant linked to Gulf War illness induces motor neuron death in mice," Neuromolecular Med., 9:83-100.
Pimenta et al., (2006), "Intranasal immunization with the cholera toxin B subunit-pneumococcal surface antigen A fusion protein induces protection against colonization with *Streptococcus pneumoniae* and has negligible impact on the nasopharyngeal and oral microbiota of mice," *Infect Immun.*, 74(8):4939-44.
Polymenidou et al., (2004), "Humoral immune response to native eukaryotic prion protein correlates with anti-prion protection," *Proc Natl Acad Sci U S A*,101 Suppl 2:14670-6.
Qin et al., (2004), "CpG ODN enhances immunization effects of hepatitis B vaccine in aged mice," Cell Mol Immunol., 1(2):148-52.
Rosado-Vallado et al., (2005), "Aluminium phosphate potentiates the efficacy of DNA vaccines against *Leishmania mexicana," Vaccine*, 23(46-47):5372-9.
Rosset et al., (2004), "Breaking immune tolerance to the prion protein using prion protein peptides plus oligodeoxynucleotide-CpG in mice," *J Immunol.*, 172(9):5168-74.
Sabirov et al., (2006), "Intranasal vaccination of neonatal mice with polysaccharide conjugate vaccine for protection against pneumococcal otitis media," *Vaccine*, 24(27-28):5584-92.
Schwarz et al., (2004), "Immunisation with a synthetic prion protein-derived peptide prolongs survival times of mice orally exposed to the scrapie agent," *Neurosci Lett.*, 350(3):187-9.
Segura-Velázquez et al., (2006), "A novel synthetic adjuvant effectively enhances the immunogenicity of the influenza vaccine," *Vaccine*, 24(8):1073-80.
Sen et al., (2006), "Immunization of aged mice with a pneumococcal conjugate vaccine combined with an unmethylated CpG-containing oligodeoxynucleotide restores defective immunoglobulin G antipolysaccharide responses and specific CD4+-T-cell priming to young adult levels," *Infect Immun.*, 74(4):2177-86.
Sigurdsson et al., (2002), "Immunization delays the onset of prion disease in mice," *Am J Pathol.*, 161(1):13-7.
Souan et al., (2001), "Modulation of proteinase-K resistant prion protein by prion peptide immunization," *Eur J Immunol.*, 31(8):2338-46.
Stewart et al., (2006), "Pre-clinical evaluation of new adjuvant formulations to improve the immunogenicity of the malaria vaccine RTS,S/AS02A," *Vaccine*, 24(42-43):6483-92.
Suckow et al., (2007), "Tissue vaccines for cancer," *Expert. Rev. Vacc.*, 6:925-937.
Suckow et al., (2008), "Use of an extracellular matrix material as a vaccine carrier and adjuvant," *Anticancer Res.*, 28(5A):2529-2534.
Sugai et al., (2005), "A CpG-containing oligodeoxynucleotide as an efficient adjuvant counterbalancing the Th1/Th2 immune response in diphtheria-tetanus-pertussis vaccine," *Vaccine*, 23(46-47):5450-6.
Süli et al., (2004), "Experimental squalene adjuvant. I. Preparation and testing of its effectiveness," Vaccine, 22(25-26):3464-9.
Sung et al., (2006), "HBV-ISS (Dynavax)," *Curr Opin Mol Ther.*, 8(2):150-5.
Theeten et al., (2005), "Effects of lowering the aluminium content of a dTpa vaccine on its immunogenicity and reactogenicity when given as a booster to adolescents," *Vaccine*, 10;23(12):1515-21.
Vitetta et al., (2006), "A pilot clinical trial of a recombinant ricin vaccine in normal humans," *Proc Natl Acad Sci U S A*, 103(7):2268-73.
Extended European Search Report for EP Application No. 07844465.0, dated Mar. 31, 2010.
International Search Report for International Application No. PCT/US07/081962, dated Apr. 17, 2008.

(56) References Cited

OTHER PUBLICATIONS

Written Opinion for International Application No. PCT/US07/081962, dated Apr. 17, 2008.
International Search Report for International Application No. PCT/US07/069727, dated Dec. 4, 2007.
Written Opinion for International Application No. PCT/US07/069727, dated Dec. 4, 2007.
International Search Report for International Application No. PCT/US09/35062, dated Jul. 22, 2009.
Written Opinion for International Application No. PCT/US09/35062, dated Jul. 22, 2009.
Allman et al., "The Th2-Restricted Immune Response to Xenogeneic Small Intestinal Submucosa Does Not Influence Systemic Protective Immunity to Viral and Bacterial Pathogens", Tissue Engineering, 2002, pp. 53-62, vol. 8(1).
Hirota, et al., "Collagen of Chronically Inflamed Skin is Over-Modified and Upregulates Secretion of Matrix Metalloproteinase 2 and Matrix-Degrading Enzymes by Endothelial Cells and Fibroblasts," The Journal of Investigative Dermatology, Dec. 2003, pp. 1317-1325, vol. 121, No. 6.
Telis, et al., "Characterizations of Collagen Fibers for Biodegradable Films Production", IUFoST World Congress, 13th World Congress of Food Science & Technology, iufost (2006). DOI:10.1051/IUFoST:20060929.
Zhang, et al., "Physicochemical Properties of Collagen, Gelatin and Collagen Hydrolysate Derived from Bovine Limed Split Wastes", Journal of the Society of Leather Technologists and Chemists., vol. 90, p. 23-28, 2006.
Folch, et al., "Microengineering of Cellular Interactions", Annu. Rev. Biomed. Eng. 02:227-256.2000.
Davis, et al., "Regulation of Tissue Injury Responses by the Exposure of Matricryptic Sites within Extracellular Matrix Molecules," American Journal of Pathology, May 2000, pp. 1489-1498, vol. 156, No. 5.
Leikina, et al., "Type I Collagen in Thermally Unstable at Body Temperature," PNAS, Feb. 5, 2002, pp. 1314-1318; vol. 99, No. 3.
German Office Action dated Jun. 28, 2011.
Higaki et al., "Collagen minipellet as a controlled release delivery system for tetanus and diphtheria toxoid", Vaccine, Apr. 30, 2001, pp. 3091-3096, vol. 19, Nos. 23-34.
Zheng et al., Wiley Interscience, 2005, pp. 61-67.
Rowley et al., "Alginate hydrogels as synthetic extracellular matrix materials", Biomaterials, Jan. 20, 1999, pp. 45-53.
Australian Office Action dated Oct. 17, 2012 in corresponding Application No. 2007345673.
U.S. Office Action dated Jan. 7, 2013 in corresponding U.S. Appl. No. 12/578,359.
Aguzzi et al., (2006), "Pathogenesis of prion diseases: current status and future outlook," *Microbiology*, 4:765-775.
Baars et al., (2000), "Skin tests predict survival after autologous tumor cell vaccination in metastatic melanoma: experience in 81 patients," *Ann. Oncol.*, 11:965-970.
Ben-Efraim et al., (2000), "Use of xenogenized (modified) tumor cells for treatment in experimental tumor and in human neoplasia," *Biomed & Pharmacotherapy*, 54:268-273.
Berd et al., (1990), "Treatment of metastatic melanoma with an autologous tumor-cell vaccine: clinical and immunologic results in 64 patients," *J. Clin. Oncol.*, 8:8158-1867.
Bergman et al., (2003), "Long-term survival of dogs with advanced malignant melanoma after DNA vaccination with xenogeneic human tyrosinase: a phase I trial," *Clin. Cancer Res.*, 9:1284-1290.
Berraondo et al., (2007), "Eradication of large tumors in mice by a tritherapy targeting the innate, adaptive, and regulatory components of the immune system," *Cancer Res.*, 67:8847-8855.
Bodey et al., (2000), "Failure of cancer vaccines: the significant limitations of this approach to immunotherapy," *Anticancer Res.*, 20:2665-2676.
Boring et al., (1993), "Cancer Statistics," *CA Cancer Journal for Clinicians*, 43:7-26.

Brooks et al., (2001), "Plasma selenium level before diagnosis and the risk of prostate cancer development," *Journal of Urology*, 166:2034-2038.
Burch et al., (2000), "Priming tissue-specific cellular immunity in a phase I trial of autologous dendritic cells for prostate cancer," *Clin. Cancer Res.*, 6:2175-2182.
Burch et al., (2004), "Immunotherapy (APC8015, Provenge) targeting prostatic acid phosphatase can induce durable remission of metastatic androgen-independent prostate cancer: a phase 2 trial," *Prostate*, 60:197-204.
Caughey et al., (2006), "Prions and their Partners in Crime," *Nature*, 443:803-810.
Chang et al., (2000), "Antigen-Specific Cancer Immunotherapy Using a GM-CSF secreting allogeneic tumor cell-based vaccine," *Int. J. Cancer*, 86:725-730.
Charles et al., (2000), "Antitumor efficacy of tumor-antigen-encoding recombinant poxvirus immunization in dunning rate prostate cancer: implications for clinical genetic vaccine development," *World J. Urol.*, 18:136-142.
Chatterjee et al., (1994), "Idiotypic antibody immunotherapy of cancer," *Cancer Immunol. Immunother.*, 38:75-82.
Corman et al., (1998), "Recognition of prostate-specific antigenic peptide determinants by human CD4 and CD8 T cells," *Clin. Exp. Immunol.*, 114:166-172.
Correale et al., (1997), "In vitro generation of human cytotoxic T lymphocytes specific for peptides derived from prostate-specific antigen," *J. Natl. Cancer Inst. USA*, 89:293-300.
Cunha et al., (2003), "Role of the stromal microenvironment in carcinogenesis of the prostate," *Int. J. Cancer*, 107:1-10.
Degruijl et al., (1999), "Cancer vaccine strategies get bigger and bigger," *Nature Medicine*, 5:1124-1125.
Denmeade et al., (2003), "Prostate specific antigen (PSA) does not affect growth of prostate cancer cells in vitro or prostate cancer xenografts in vivo," *Prostate*, 56:45-53.
Dillman et al., (1998), "Clinical experience with autologous tumor cell lines for patient-specific vaccine therapy in metastatic melanoma," *Cancer Biother. Radiopharm.*, 13:165-173.
Dillman et al., (2001), "Short-term cell lines from breast cancer for use as autologous tumor cell vaccines in the treatment of breast cancer," *Cancer Biotherapy & Radiopharmaceuticals*, 16:205-211.
Dols et al., (2003), "Vaccination of women with metastatic breast cancer using a costimulatory gene (CD80)-modified, HLA-A2 matched allogeneic, breast cancer cell line: clinical and immunological results," *Human Gene Therapy*, 14:1117-1123.
Donnelly, (2003), "Cancer vaccine targets leukemia," *Nature Medicine*, 9:1354-1356.
Eaton et al., (2002), "Allogeneic whole-cell vaccine: a phase I/II study in men with hormone-refractory prostate cancer," *British Journal of Urology*, 89:19-26.
Ezzell, (1995), "Cancer 'vaccines': an idea whose time has come?" *J. NIH Res.*, 7:4-49.
Fernandez-Acenero et al., (2002), "Prognostic influence of tumor-associate eosinophilic infiltrate in colorectal carcinoma," *Cancer*, 88:1544-1548.
Fong et al., (2001), "Dendritic cell-based xenoantigen vaccination for prostate cancer immunotherapy," *J. Immunol.*, 167:7150-7156.
Forni et al., (2000), "Immunoprevention of cancer," *Cancer Res.*, 60:2571-2575.
Frost et al., (1975), "Tumor immunoprophylaxis in mice using glutaraldehyde-treated syngenic tumor cells," *Cancer Res.*, 35:2646-2650.
Fuessel et al., (2006), "Vaccination with hormone-refractory prostate cancer patients with peptide cocktail-loaded dendritic cells: results of phase I clinical trial," *Prostate*, 66:811-821.
Furbert-Harris et al., (2003), "Inhibition of prostate cancer cell growth by activate eosinophils," *The Prostate*, 57:165-175.
Gann et al., (1999), "Lower prostate cancer risk in men with elevated plasma lycopene levels: results of a prospective analysis," *Cancer Research*, 59:1225-1230.
Gann et al., (1999), "Lower prostate cancer risk in men with elevated plasma lycopene levels: results of a prospective analysis," *JAMA*, 281:1682.

(56) References Cited

OTHER PUBLICATIONS

Granziero et al., (1999), "Adoptive immunotherapy prevents prostate cancer in a transgenic animal model," *Eur. J. Immunol.*, 29:1127-1138.

Griffith et al., (2001), "Inhibition of murine prostate tumor growth and activation of immunoregulatory cells with recombinant canarypox viruses," *J. Natl. Cancer Inst.*, 93:998-1007.

Gulley et al., (2002), "Phase I study of a vaccine using recombinant vaccinia virus expressing PAS (rV-PSA) in patients with metastatic androgen-independent prostate cancer," *The Prostate*, 53:109-117.

Hahn et al., (2006), "Short-term dietary administration of celecoxib enhances the efficacy of tumor lysate-pulsed dendritic cell vaccines in treating murine breast cancer," *Int. J. Cancer*, 118:2220-2231.

Harada et al., (2003), "Prostate-specific antigen-derived epitopes capable of inducing cellular humoral responses in HLA-A24+ prostate cancer patients," *Prostate*, 57:152-159.

He et al., (2003), "Inhibition of tumor growth with a vaccine based on xenogeneic homologous fibroblast growth factor receptor-1 in mice," *J. Biol. Chem.*, 24:21831-21836.

Horiguchi et al., (2002), "Screening of HLA-A24-restricted epitope peptides from prostate-specific membrane antigen that induces specific antitumor cytotoxic T lymphocytes," *Clin. Cancer Res.*, 8:3885-3892.

Hrouda et al, (1998), "*Mycobacterium vaccae* (SRL172): a potential immunological adjuvant elevated in rate prostate cancer," 82:870-876.

Hrouda et al., (2000), "Allogeneic whole-tumor cell vaccination in the rat model of prostate cancer," *BJU International*, 86:742-748.

Hursting et al., (1990), "Types of dietary fat and the incidence of cancer at five sites," *Preventive Medicine*, 19:242-253.

Jager et al., (2003), "Antigen-specific immunotherapy and cancer vaccines," *Intl. J. Cancer*, 106:817-820.

Jarvinen et al., (2000), "Intranasal vaccination of New Zealand white rabbits against pasteurellosis using alginate-encapsulated *Pasteurella multocida* toxin and potassium thiocyanate extract," *Comparative Medicine*, 50:263-269.

Jocham et al., (2004), "Adjuvant autologous renal tumour cell vaccine and risk of tumour progression in patients with renal-cell carcinoma after radical neprectomy: phase III, randomised controlled trial," *Lancet*, 363:594-599.

Kobayashi et al., (2003), "Identification of naturally processed helper T-cell epitopes from prostate-specific membrane antigen using peptide-based in vitro stimulation," *Clin. Cancer Res.*, 9:5386-5393.

Kochenderfer et al., (2007), "Maximizing CD8+ T cell responses elicited by peptide vaccines containing CpG oligodeoxynucleotides," *Clin. Immunol.*, 124:119-130.

Lee et al., (1999), "Increased vaccine-specific T cell frequency after peptide-based vaccination correlates with increased susceptibility to in vitro stimulation but does not lead to tumor regression," *J. Immunol.*, 163:6292-6300.

Li et al., (2008), "IL-21-mediated Foxp3 suppression leads to enhanced generation of antigen-specific CD8+ T lymphocytes," *Blood*, 111:229-235.

Lord et al., (2007), "Low dose metronomic oral cyclophosphamide for hormone resistant prostate cancer: a phase II study," *J. Urology*, 177:2136-2140.

Lu et al., (2002), "Rcognition of prostate tumor cells by cytotoxic T lymphocytes specific for prostate-specific membrane antigen," *Cancer Res.*, 62:5807-5812.

Lubaroff et al., (2006), "Decreased cytotoxic T cell activity generated by co-administration of PSA vaccine and CpG ODN is associated with increased tumor protection in a mouse model of prostate cancer," *Vaccine*, 24:6155-6162.

Matsueda et al., (2005), "Identification of peptide vaccine candidates for prostate cancer patients with HLS-A3 super-type alleles," *Clin. Cancer Res.*, 11:6933-6943.

McNeel et al., (2001), "Identification of T helper epitopes from prostatic acid phosphatae," *Cancer Res.*, 61:5161-5167.

Miller et al., (2006), "The role of melatonin in immuno-enhancement: potential application in cancer," *Int. J. Exp. Path.*, 87:81-87.

Moody et al., (1994), "Interleukin-2 transfected prostate cancer cells generate a local antitumor effect in vivo," *Prostate*, 24:244-251.

Nomura et al., (2000), "Serum selenium and subsequence risk of prostate cancer," *Cancer Epidemiology, Biomarkers & Prevention*, 9:883-887.

Ochsenbein et al., (1999), "Immune surveillance against a solid tumor fails because of immunological ignorance," *Proc. Natl. Acad. Sci. USA*, 96:2233-2238.

Ohashi et al., (2000), "Significance of tumor associate eosinophilia and other inflammatory cell infiltrate in early esophageal squamous cell carcinoma," *Anticancer Res.*, 20:3025-3030.

Okaji et al., (2004), "Vaccination with autologous endothelium inhibits angiogenesis and metastasis of colon cancer through autoimmunity," *Cancer Science*, 95:85-90.

Ou et al., (2008), "Enhancement of dendritic cell-tumor fusion vaccine potency by indoleamine-pyrrole 2,3-dioxygenase inhibitor, 1-MT," *J. Cancer Res. Clin Oncol.*, 134:525-533.

Peters et al., (1979), "Preparation of immunotherapeutic autologous tumor cell vaccines from solid tumors," *Cancer Res.*, 39:1353-1360.

Pollard et al., (1975), "Transplantable metastasizing prostate adenocarcinomas in rats," *J. Natl. Cancer Inst.*, 54:643-649.

Pollard et al., (1986), "Production of autochthonous prostate cancer in Lobund-Wistar rats by treatments with N-Nitroso-N-methylurea and testosterone," *J. Natl. Cancer Inst.*, 77:583-587.

Pollard et al., (1987), "Autochthonous prostate cancer in Lobund-Wistar rats; a model system," *The Prostate*, 11:219-227.

Pollard et al., (2006), "Dietary prevention of hormone refractory prostate cancer in Lobund-Wistar rats: a review of studies in relevant animal model," *Comp. Med.*, 56:461-467.

Pollard, (1998), "Lobund-Wistar rat model of prostate cancer in man," *The Prostate*, 37:1-4.

Ringler et al., (1985), "Protection of rabbits against experimental pasteurellosis by vaccination with a potassium thiocyanate extract of *Pasteurella multocida*," *Infection & Immunity*, 49:498-504.

Ruozi et al., (2007), "Intact collagen and atelocollagen sponges: Characterization and ESEM observation," *Mat. Sci. Eng.*, 27:802-810.

Simons et al., (1999), "Induction of immunity to prostate cancer antigens: results of a clnical trial of vaccination with irradiated autologous prostate tumor cells engineered to secrete granulocyte-macrophage colony-stimulating factor using ex vivo gene transfer," *Cancer Res.*, 59:5160-5168.

Simons et al., (2002), "Phase II trials of a GM-CSF genetransduced prostate cancer cell line vaccine (GVAX) in hormone refractory prostate cancer," *Proc. Am. Soc. Clin. Oncol.*, 21:183a (Abstract 729).

Singh et al., (1992), "Stroma is critical for preventing or permitting immunological destruction of antigenic cancer cells," *J. Exp. Med.*, 175:139-146.

Small et al., (2000), "Immunotherapy of hormone-refractory prostate cancer with antigen-loaded dendritic cells," *J. Clin. Oncol.*, 18:3894-3903.

Small et al., (2005), "Results of a placebo-controlled phase III trial of immunotherapy with APC8015 for patients with homrone refractory prostate cancer (HRPC)," *Proc. Am. Soc. Clin. Oncol.*, 23(16S):378S (Abstract 4500).

Srinivasan et al., (2004), "Tumor antigens for cancer immunotherapy: therapeutic potential of xenogeneic DNA vaccines," *J. Translational Med.*, 2:1-12.

Stack et al., (1982), "Autologous X-irradiated tumor cells and percutaneous BCG in operable lung cancer," *Thorax*, 37:599-593.

Suckow et al., (1991), "Heat-labile toxin-producing isolates of *Pasteurella multocida* from rabbits," *Lab. Animal Sci.*, 41:151-156.

Suckow et al., (2007), "Prevention of human PC-346C prostate cancer growth in mice by xenogeneic tissue vaccine," *Cancer Immunol. Immunother.*, 56:1275-1283.

Tjoa et al., (1999), "Follow-up evaluation of a phase II prostate cancer vaccine trial," *The Prostate*, 40:125-129.

Tjoa et al., (2000), "Development of a dendritic cell-based prostate cancer vaccine," *Immunology Letters*, 74:873-893.

Vermorken et al., (1999), "Active specific immunotherapy for stage II and stage III human colon cancer: a randomized trial," *Lancet*, 353:345-350.

(56) References Cited

OTHER PUBLICATIONS

Vieweg et al., (1994), "Immunotherapy of prostate cancer in the Dunning rate model: use of cytokine gene modified tumor vaccines," *Cancer Res.*, 54:1760-1765.

Wang et al., (1993), Lack of HLA class I antigen expression by melanoma cells SK-Mel-33 caused by reading a frameshift in β2-Microglobulin Messenger RHNA,: *J. Clin. Invest.*, 91:648-692.

Wei et al., (2002), "Immunotherapy of tumors with vaccines based on xenogeneic homologous molecules," *Anti-Cancer Drugs*, 13:229-235.

Xue et al., (1997), "Induction of human cytotoxic T lymphocytes specific for prostate-specific antigen," *Prostate*, 30:73-78.

Zhang et al., (2003), "Dendritic cells transfected with interleukin-12 and pulsed with tumor extract inhibit growth of murine prostatic carcinoma in vivo," *Prostate*, 55:292-298.

Nakaoka et al., Potentiality of gelatin microsphere as immunological adjuvant, Vaccine, 1995, pp. 653-661, vol. 13, No. 7, Elsevier Science, Ltd., Great Britain.

Teir et al., (1957), "Effects of intraperitoneally injected suspension of roetgen irradiated and non-irradiated tumor tissue on the growth of homologous tissue," Acta Pathol. Microbiol. Scand., 40:273-282.

Badylak, Stephen F., Small Intestinal Submocosa Burkauser Publishers (1993), Presented at the Tissue Engineering Symposium in Keystone, Colorado, Apr. 1992.

Ball et al., (2005), Clin. Cancer Res., 11:4469-4478.

Brown-Etris, Marie, et al. Wounds: Part I: A New Biomaterial Derived from Small Intestine Submucosa and Developed ino a Wound Matrix Device, Available online at www.woundresearch.com (Oct. 25, 2006).

DM, Wu T. (2000), Int J Cancer., 86(5):725-20.

U.S. Office Action issued in co-pending U.S. Appl. No. 12/868,908 dated Apr. 4, 2013.

* cited by examiner

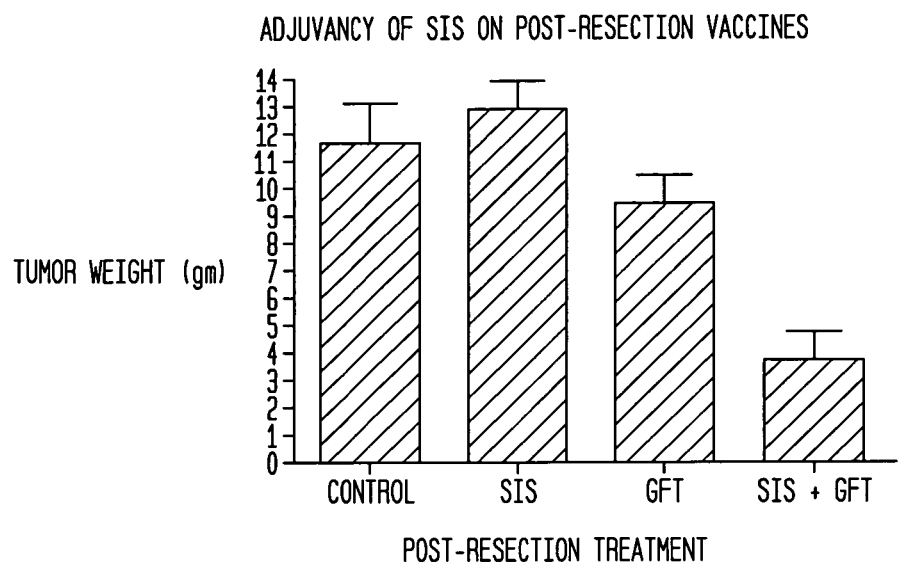
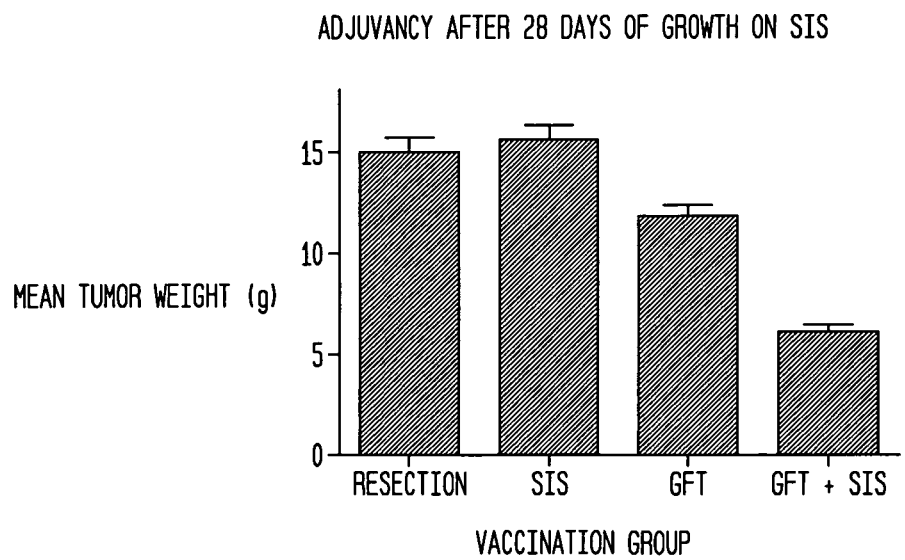

ly known antibodies to diphtheria and tetanus toxins is well established and HBsAg vaccine has been adjuvinated with

EXTRACELLULAR MATRIX CANCER VACCINE ADJUVANT

CROSS-REFERENCE TO RELATED APPLICATIONS

This application makes reference to the following provisional U.S. Patent Application No. 60/730,379 entitled "Use of Extracellular Matrix Materials as a Vaccine Carrier and Adjuvant", filed Oct. 27, 2005, and to U.S. Ser. No. 11/209, 766, entitled "Tissue Vaccines and Uses Thereof", filed Aug. 24, 2005. The entire disclosure and contents of the above applications are hereby incorporated by reference herein.

STATEMENT OF JOINT RESEARCH AGREEMENT

In compliance with 37 C.F.R. §1.71(g) (1), disclosure is herein made that the claimed invention was made pursuant to a Joint Research Agreement as defined in 35 U.S.C. 103 (c) (3), that was in effect on or before the date the claimed invention was made, and as a result of activities undertaken within the scope of the Joint Research Agreement, by or on the behalf of the University of Notre Dame and Cook Biotech, Inc. (West Lafayette, Ind.).

BACKGROUND

1. Field of the Invention

The present invention relates generally to cancer vaccines that include an adjuvant, and to cancer vaccine adjuvants alone. In particular, the invention relates to cancer vaccine adjuvants derived or obtained at least in part from biological tissues, particularly extracellular matrix materials, such as from the small intestinal mucosa. The invention also relates to the field of methods for immunizing an animal against cancer using a cancer vaccine preparation that includes an extracellular matrix tissue-derived adjuvant. The invention also relates to the field of methods for preparing cancer vaccine adjuvants, as a method for preparing a cancer vaccine adjuvant from extracellular matrix tissue for vaccines to immunize an animal against cancer, particularly prostate cancer, is provided.

2. Related Art

Vaccination for the treatment of cancer is receiving increasing attention. Vaccines for melanoma, prostate and breast cancers have undergone development to include human clinical trials. Most of these vaccines utilize specific proteins to directly immunize the patient or to pulse harvested dendritic cells prior to infusion into the patient. Some trials have also used inactivated allogenic cancer cells grown in vitro.

In general, cancer vaccines have been administered without an adjuvant or with specific cytokines included as adjuvants. An adjuvant is defined as a compound which enhances the immune response to a vaccine immunogen(s).

There have been some reports of the use of a mycobacterial adjuvant with normal non-malignant cells. For example, use of human prostate cells in the treatment of prostate cancer is described in U.S. Pat. No. 6,972,128 (Dalgleish et al.). In particular, an allogeneic immunotherapeutic agent containing immortalized normal (non-malignant) human prostate cells (replication incompetent) is described. A mycobacterial adjuvant was used with a non-malignant murine melanoma cell preparation in a vaccine suitable for intra-dermal injection. These preparations were reported to provide some protection against murine tumor cell growth.

A combination of aluminum hydroxide and aluminum phosphate (collectively referred to as alum) is currently used in commercial vaccines as adjuvants for human and veterinary applications (11, 12). The efficacy of alum in increasing antibody responses to diphtheria and tetanus toxins is well established and HBsAg vaccine has been adjuvinated with alum. While the usefulness of alum is well established for some applications, it has limitations. For example, alum is ineffective for influenza vaccination and inconsistently illlicits cell mediated immune response. The antibodies elicited by alum-adjuvinated antigens are mainly of the IgG1 isotype in the mouse, which may be optimal for protection by some vaccinal agents.

Bacterial vaccines have also been described that include an adjuvant, typically alum. Because alum is particularly efficient at stimulating Th2 antibody responses to co-administered immunogens, and because effective cancer immunity relies heavily on Th1 cell-mediated immunity, alum is not typically included in cancer vaccines. Clearly, cancer vaccination would benefit from a method to provide general enhancement of the immune response to cancer immunogens.

Noscapine has been described as an adjuvant for vaccines, as well as for use in the treatment of tumors and cancer, in U.S. Pat. No. 7,090,852. Noscapine is an alkaloid from opium, and is available as a commercial byproduct in the commercial production of prescription opiates.

Recombinant, single immunogen cancer vaccines have also been described. One such product in Phase 3 clinical trials is the GVAX® vaccine (Cell Genesys, Inc., South San Francisco, Calif.). This cancer vaccine is used in patients with advanced-stage, hormone-refractory prostate cancer, and is comprised of two allogeneic prostate cancer cell lines that have been genetically modified to secrete granulocyte-macrophage colony stimulating factor (GM-CSF). This hormone plays a role in stimulating the body's immune response to the cancer vaccine. The cells are irradiated for safety (3). Cancer vaccination with the GVAX product has demonstrated a median increases in survival in cancer patients receiving the vaccine of approximately 7 months (4).

Though some studies have utilized specific cytokines as cancer vaccine adjuvants, such as GM-CSF in the GVAX vaccine (4), those cytokines typically enhance only specific features of the immune response and may be unstable outside of very controlled storage conditions (13, 14).

Pure soluble, recombinant and synthetic antigens, despite their better tolerability, are unfortunately often much less immunogenic than live or killed whole organism vaccines. Thus, the move towards the development of safer subunit vaccines has created a major need for more potent adjuvants. In particular, there is an urgent need for adjuvants capable of boosting cellular (Th1) immunity with a more acceptable toxicity.

Despite the description of over one hundred adjuvants in the scientific literature, alum remains the only adjuvant approved for human use in the USA (Petrovsky, 2006). Unfortunately, alum has no effect on cellular immunity and is faced with increasing concerns regarding potential for cumulative aluminium toxicity. There is a major unmet need for a safe efficacious adjuvant capable of boosting cellular plus humoral immunity.

The prerequisites for an ideal cancer adjuvant differ from conventional adjuvants for many reasons. First, the patients that will receive the vaccines are immuno-compromised because of, for example, impaired mechanisms of antigen presentation, non-responsiveness of activated T cells and enhanced inhibition of self-reactivity by regulatory T cells. Second, the tumor antigens are usually self-derived and are, therefore, poorly immunogenic. Third, tumors develop escape mechanisms to avoid the immune system, such as tumor immunoediting, low or non-expression of MHC class I molecules or secretion of suppressive cytokines. Thus, adjuvants for cancer vaccines need to be more potent than for prophylactic vaccines, and consequently may be more toxic, and may even induce autoimmune reactions.

To heighten the immune response to cancer antigens, researchers often attach a decoy substance, or adjuvant, that the body will recognize as foreign. Such adjuvants are often proteins or bacteria which "trick" the immune system into mounting an attack on both the decoy and the tumor cells. Other adjuvants act to stimulate specific effector cells within the immune system. Several adjuvants are described below:

Keyhole limpet hemocyanin (KLH) is a protein made by a shelled sea creature found along the coast of California and Mexico known as a keyhole limpet. KLH is a large protein that both causes an immune response and acts as a carrier for cancer cell antigens (Bandandi, et al, 2006(52); Redfern et al, 2006(53)). Cancer antigens often are relatively small proteins that may be invisible to the immune system. KLH provides additional recognition sites for immune cells known as T-helper-cells and may increase activation of other immune cells known as cytotoxic T-lymphocytes (CTLs).

Bacillus Calmette Guerin (BCG) is an inactivated form of the tuberculosis bacterium. BCG is added to some cancer vaccines with the hope that it will boost the immune response to the vaccine antigen (Totterman, 2005(54); Mosolits, 2005 (55)). It is not well understood why BCG may be especially effective for eliciting immune response. However, BCG has been used for decades with other vaccines, including the vaccine for tuberculosis.

Interleukin-2 (IL-2) is a protein made by the body's immune system that may boost the cancer-killing abilities of certain specialized immune system cells called natural killer cells. Although it can activate the immune system, many researchers believe IL-2 alone will not be enough to prevent cancer relapse. Several cancer vaccines use IL-2 to boost immune response to specific cancer antigens (Wei, 2006 (57); He, 2005 (56), Rousseau, 2006(58)).

Granulocyte Monocyte-Colony Stimulating Factor (GM-CSF) is a protein that stimulates the proliferation of antigen-presenting cells and has been used as an adjuvant in a prostate cancer vaccine (Simons, 2006 (59)).

SIS is a commercially available accellular extracellular matrix (ECM) preparation produced from porcine small intestinal submucosa. SIS is a naturally derived, extracellular matrix, that is not synthetic or cross-linked. A commercial form of this collagenous acellular material is available from Cook Biotech, and is known by the trade name, "Oasis®". In this product, SIS is taken from a biological source and is processed to remove all cells. This product is biocompatible and safe for human use.

SIS has found substantial utility as a tissue growth scaffold. For example, SIS has shown wide utility in urology (15-22), wound care and repair (23-24), as an anal fistula plug (25), tendon repair, and bone healing (26-27, 29, 31-33). Following implantation, SIS rapidly attracts mononuclear inflammatory cells followed by ingrowth of host tissue (FIG. 1). In this way, SIS serves as a scaffold for tissue repair (26-28). The SIS then becomes fully replaced by host tissue. Other extracellular matrices, such as porcine renal capsule material, behave in a similar fashion to SIS (29-30).

Canine prostate cancer cells have been reported to maintain their invasive phenotype when grown on SIS in culture (44). Studies in Lobund-Wistar rats have shown that SIS does not inherently promote growth of cancer in vivo (39). Despite these observations, SIS has not been proposed in any anti-cancer applications.

A need continues to exist in the medical arts for materials that may be used to enhance and/or improve existing clinical alternatives to the treatment of cancer, particularly to improve existing forms of cancer vaccines and cancer vaccine adjuvants with improved immunogenicity.

SUMMARY

The present invention was developed in part by the inventors' recognition of the robust inflammatory response invoked by a material used in tissue repair known as SIS. From these observations, the inventors harnessed the inflammatory-provoking activity of SIS, and other materials prepared with SIS, in the design of a highly immunopotent cancer vaccine preparation and cancer adjuvant. While completely divorced from the field of tissue repair materials, the crafting of cancer vaccine preparations using SIS and materials like it resulted in the design of the herein described cancer treatment and vaccination formulations prepared from extracellular matrix materials.

The present invention is unique in the respect that, among other things, it involves the modification and use of a three-dimensional extracellular matrix material, SIS, and modified preparations thereof, to grow and expand tumor cells, and the use of these cultured tumor cells in an anti-cancer adjuvant.

Cancer Vaccine Adjuvant

In one aspect, the present invention provides an extracellular matrix (ECM) material, such as a modified preparation of SIS, FEM, RCM, or other appropriate extracellular matrix material of choice, as a cancer vaccine adjuvant. In some embodiments, these preparations may be described as essentially free of alum. In other embodiments, the ECM materials may be described as a modified preparation of SIS, FEM, RCM, or other extracellular matrix material of choice (diluted) about 2-fold to about 20-fold, or from 5-fold to about 10-fold. In some embodiments, a standard SIS material, such as that obtained from a commercial vendor, is diluted about 1-10 fold, and in this dilution, is particularly well suited for use as an injectable vaccine material. In particular embodiments, the extracellular material is diluted in a physiologically acceptable solution, such as saline.

Cancer Vaccine

In another aspect, the present invention provides a cancer vaccine comprising a preparation of an extracellular matrix tissue together with a preparation of (replication incompetent) tumor cells. In some embodiments, the tumor cells are prostate cancer cells, breast cancer cells, liver cancer cells, lung cancer cells, colon cancer cells, etc. In particular embodiments, the tumor cells are treated so as to render them replication incompetent by fixing the cells with glutaraldyhyde. This glutaraldyhyde preparation of tumor cells may then be mixed with the extracellular matrix material, such as SIS.

In one aspect of the invention, there is provided a composition comprising an immuno-enhancing preparation of an extracellular matrix material, particularly the extracellular matrix of the small intestinal submucosa (SIS) or tissue of the renal capsule. In some embodiments, the extracellular matrix comprises a menu of antigenic species characteristic of porcine small intestinal submucosa. This preparation may also be described as comprising a small intestinal submucosa tissue preparation, or purified preparation thereof.

According to another aspect, there is provided a composition comprising an adjuvant and a vaccine of interest. In some embodiments, the vaccine is a whole-cell vaccine. In some embodiments the vaccine may be described as a cancer vaccine. In other embodiments, the vaccine comprises an immunogenic amount of a tumor antigen preparation of interest; and a cancer adjuvant, wherein said cancer adjuvant comprises a preparation characteristic of an extracellular matrix material, and wherein the immunogenic amount of the tumor antigen preparation of interest sufficient to stimulate a protective response in the presence of the cancer adjuvant is less than the amount of the tumor antigen preparation of interest sufficient to stimulate a protective response in the absence of the cancer adjuvant.

Method of Preparing a Cancer Vaccine Adjuvant and a Cancer Vaccine

According to another broad aspect of the invention, there is provided a method for preparing a cancer vaccine adjuvant. In some embodiments, the method comprises obtaining an amount of small intestinal submucosa (SIS) or other extracellular matrix material of choice (FEM, RCM), and preparing a processed preparation thereof suitable for use as a cancer vaccine adjuvant in combination with an immunogenic amount of a whole cell antigen vaccine preparation, such as prostate cells.

In another aspect, the invention provides a method for preparing a cancer vaccine. In some embodiments, the method comprises preparing a cancer vaccine adjuvant as described, and combining the cancer vaccine adjuvant with an immunogenic amount of a cancer antigen of interest. In some embodiments, the immunizing antigen of interest is a tumor cell preparation, such as a prostate, lung, breast, colon, or other cancer cell preparation. In some embodiments, the prostate cancer cell preparation comprises prostate tumor cells harvested from an animal that have been treated and/or processed with glutaradyhyde.

Methods of Treating/Inhibiting/Immunizing an Animal Against Cancer

According to yet another broad aspect of the invention, a method for treating and/or immunizing an animal having cancer or at risk of developing cancer is provided. In some embodiments, the method comprises immunizing an animal against prostate, breast, colon, lung, or other cancer of interest, employing as antigen a tumor tissue comprising the specific type of cancer cells of interest. In particular embodiments, the method provides for the treatment and/or immunization of a human having or at risk of developing prostate cancer. The present invention provides for both a human vaccine and an animal vaccine.

In some embodiments, the method for treating prostate cancer employs a composition comprising a vaccine, the vaccine comprising an adjuvant composed of an extracellular matrix (ECM) material together with a tissue preparation, such as a glutaraldehyde-fixed xenogeneic tissue preparation of prostate cancer cells. These preparations are found to be more immunogenic than use of the glutaraldyhyde fixed xenogenic tissue preparation without the extracellular matrix material adjuvant.

Method of Expanding a Tumor Cell Population

In yet another aspect, the invention provides a method for expanding a population of tumor and/or cancer cells in vitro. These cancer and/or tumor cells may then be used as an antigen of interest to be included with an extracellular matrix material adjuvant to provide a cancer vaccine as described herein.

Clinical Cancer Treatment Preparations

In yet another aspect, the invention provides a variety of unique clinical cancer treatment preparations. In some embodiments, these cancer treatment preparations may take the form of a gel, a sheet, or an injectable preparation of an extracellular matrix material. The injectable preparations may be further described as suitable for i.v. administration.

The following abbreviations are used throughout the description of the present invention:
  ECM—Extracellular Matrix;
  FEM Fascia Extracellular Matrix Material;
  GFT—Glutaraldehyde Fixed Tumor;
  LW Rat—Lobund-Wistar rat;
  MEM—Modified Eagle's Medium;
  PAIII—Prostate Adenocarcinoma III Cell Line from LW rats;
  RCM—Renal Capsule Material;
  SIS—Small Intestinal Submucosa;

BRIEF DESCRIPTION OF THE DRAWINGS

The invention will be described in conjunction with the accompanying drawings, in which:

FIG. 5, according to one embodiment of the invention, demonstrates the adjuvancy of GFT cell vaccine on SIS after three days of growth in culture. Cells harvested from PAIII rat tumors were grown on SIS for three days. This cell population includes neoplastic epithelium, endothelial cells, fibroblasts and other connective tissue. Subcutaneous PAIII tumors were surgically resected and the GFT cell vaccine; GFT cell vaccine on SIS; or SIS without added cells placed onto the tumor bed. Rats were euthanized three weeks later and tumor weighed. Bars represent mean group tumor weight (±standard deviation). A significant ($P \leq 0.01$) reduction in mean tumor weight was found in rats vaccinated with the GFT cell vaccine on SIS compared to all other groups.

FIG. 6, according to one embodiment of the invention, demonstrates the ajuvancy of GFT cell vaccine on SIS after 28 days of growth in culture. Cells harvested from PAIII rat tumors were grown on SIS for 28 days. This cell population includes neoplastic epithelium, endothelial cells, fibroblasts and other connective tissue. Subcutaneous PAIII tumors were surgically resected and the GFT cell vaccine; GFT cell vaccine on SIS; or SIS without added cells placed onto the tumor bed. Rats were euthanized three weeks later and tumor weighed. Bars represent mean group tumor weight (±standard deviation). A nearly significant ($P \leq 0.053$) reduction in mean tumor weight was found in rats vaccinated with the GFT cell vaccine on SIS compared to rats vaccinate with the GFT cell vaccine alone; however the difference was significant (P≤0.01) compared to groups undergoing only resection or resection plus administration of SIS with no added cells.

DETAILED DESCRIPTION

Figure 1:
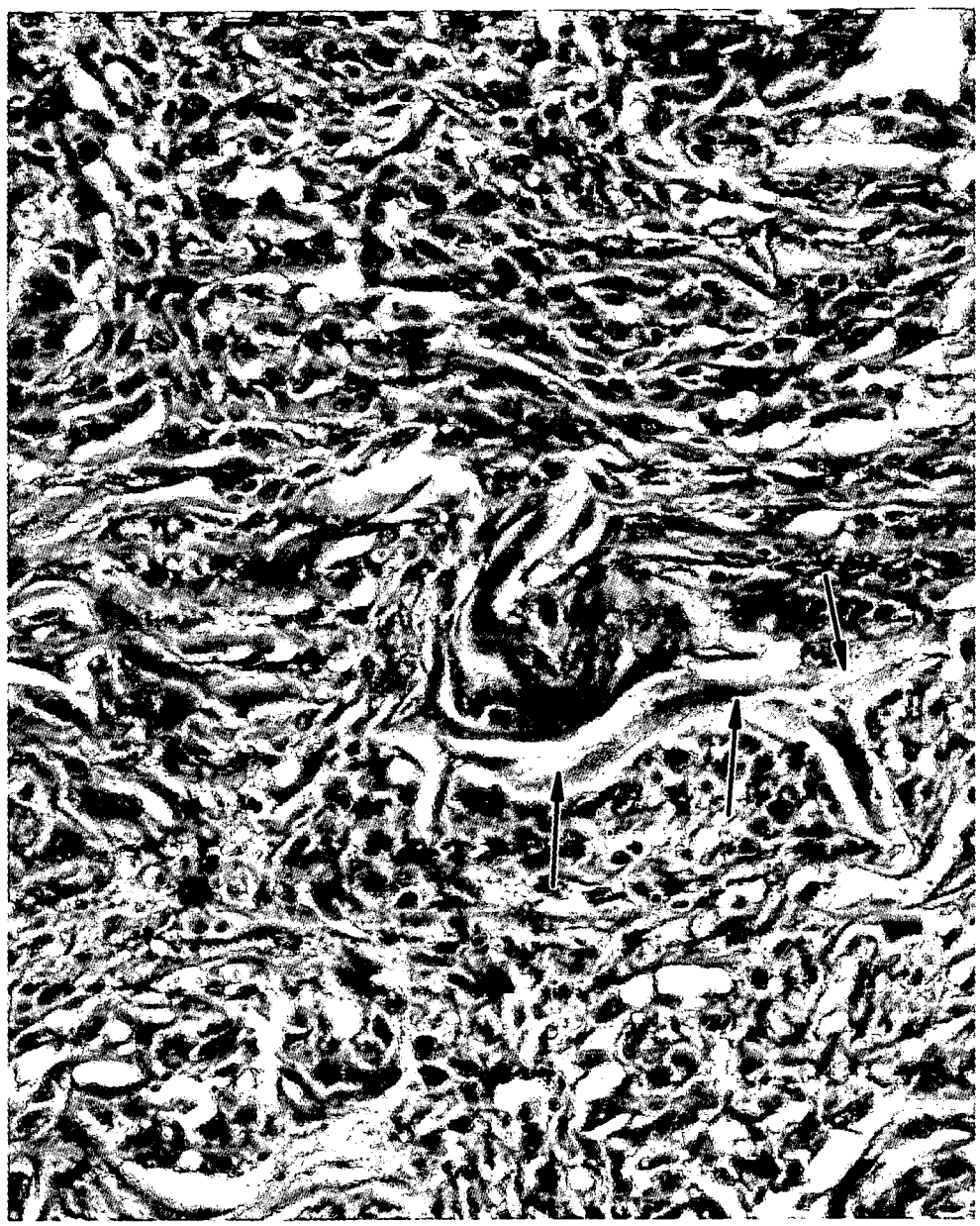
FIG. 1, according to one embodiment of the present invention, presents a remnant of SIS extracellular matrix material in a rat 28 days after surgical implantation. The remaining biomaterial is surrounded by macrophages with occasional lymphocytes. Stained with H & E, 400×.

It is advantageous to define several terms before describing the invention. It should be appreciated that the following definitions are used throughout this application.

DEFINITIONS

Where the definition of terms departs from the commonly used meaning of the term, applicant intends to utilize the definitions provided below, unless specifically indicated.

For the purposes of the present invention, the term "adjuvant" is defined as a substance which enhances the immune response to an immunogen.

For purposes of the present invention, the term, "adjuvancy" is defined as the ability of an agent to enhance and/or promote the immune response of animal to a particular antigen.

For the purposes of the present invention, the term "biosynthetic material" is defined as a material that is in part or whole made up from or derived from a biological tissue.

For purposes of the present invention, the term "biological tissue" is defined as an animal tissue, including human, or plant tissue that is or that once was (cadaver tissue, for example) part of a living tissue or organism.

For the purposes of the present invention, the term "extracellular matrix" is defined as a tissue derived or bio-synthetic material that is capable of supporting the growth of a cell or culture of cells.

For the purposes of the present invention, the term "cancer vaccine" is defined as any preparation capable of being used as an inoculation material or as part of an inoculation material, that will provide a treatment for, inhibit and/or convey immunity to cancer and/or tumor growth.

For the purposes of the present invention, the term "immunize" is defined as eliciting an immune response in an animal, both a humoral immune response and a cellular immune response.

For the purposes of the present invention, the term "immune provoking amount" is defined as an amount of the antigen required to elicit an immune response in the animal.

DESCRIPTION

The description of the present invention is enhanced by the various examples that follow.

Example 1

Materials and Methods

The present example provides some examples of materials and methods that may be used in the practice of the present invention.

Small Intestinal Submucosa (SIS)

Small Intestinal Submucosa (SIS) was obtained from Cook Biotech, Inc. (West Lafayette, Ind.). The material was provided as a sterile, lyophilized sheet of extracellular matrix. Experimental grade material was provided for use in the present studies of an SIS preparation that was described as having been prepared by harvesting porcine jejunum and placing 10- to 20-cm lengths into saline solution (31-33). Following removal of all mesenteric tissues, the jejunal segment was everted and the tunica mucosa abraded using a longitudinal wiping motion with a scalpel handle and moistened gauze. The serosa and tunica muscularis were then gently removed using the same procedure. The remaining tissue was disinfected with peracetic acid, rinsed extensively in high purity water, and sterilized using ethylene oxide prior to implantation.

Renal Capsule Material (RCM)

RCM was obtained from Cook Biotech, Inc. (West Lafayette, Ind.). Briefly, renal capsule was dissected from mature pig kidneys immediately following slaughter. It was thoroughly rinsed under running tap water and disinfected using a dilute solution of peracetic acid in ethanol to remove potential contaminating bacteria and viruses (34). Following disinfection, the RCM was rinsed in high purity water to remove the acid, lyophilized into a sheet form, and subsequently sterilized prior to implantation using ethylene oxide gas.

PAIII Cells—

The PAIII cell line was derived from an authochthonous prostate tumor of an LW rat. PAIII cells have been transplanted into LW rats for many passages with no change in pattern of growth or disease. When PAIII cells are transplanted subcutaneously into the flank of LW rats, large, metastasizing adenocarcinomas develop within 40 days, though initial tumors are palpable within 10 days. From the primary tumor, the PAIII cells metastasize spontaneously to the lungs. PAIII tumors are hormone-independent and refractory to most treatments (35).

GFT Cell Vaccine

GFT cell vaccine was a glutaraldehyde-fixed tumor (GFT) suspension of cells harvested from tumors grown in animals. GET cell vaccine was prepared from tumor tissue (36). Specifically, three grams of a subcutaneous tumor tissue was harvested from a Lobund-Wistar rat and used in the vaccine preparation. The subcutaneous tumor had been produced by administering prostate adenocarcinoma cells isolated from an autochthonous, metastatic prostate adenocarcinoma in a LW rat (37).

The tissue was finely minced, repeatedly aspirated with a 1 cc syringe, and an aliquot drawn with a 20-gauge needle to eliminate large aggregates to create a cell suspension in modified Eagle's medium (MEM). The cell suspension was incubated in 2.5% glutaraldehyde (v/v) at 37° C. for 120 minutes and then washed thoroughly with media to produce the GFT cell preparation.

Animals

LW rats obtained from a breeding colony maintained at the University of Notre Dame were used for all studies. In this model, large tumors develop subcutaneously following subcutaneous administration of $1\times10^6$ PAIII cells in approximately 99% of rats.

Subcutaneous Tumor and Tumor Resection Model

In this model, male, 3-4 month old LW rats are administered $1\times10^6$ PAIII cells subcutaneously into the flank. After 14-21 days, a palpable tumor is present, and by 40 days metastatic foci are present in the lungs. For studies involving resection, the animal is prepared for aseptic surgery. The visible tumor is resected, though the resection is not radical and sufficient tumor bed presumably remains, as tumor regrowth occurs in 100% of untreated individuals.

Growth of Cells on SIS and RCM

Sheets of single-layer SIS or RCM are cut into 2×2 cm sections and placed into Modified Eagle's Medium (MEM). PAIII cells ($1\times10^6$) or cells ($1\times10^6$) harvested directly from a PAIII subcutaneous rat tumor are layered on the SIS or RCM and incubated at 37° C. To create the GFT cell vaccine on SIS, the SIS with attached cells then undergoes glutaraldehyde fixation (GFT) and washing. Glutaraldehyde fixation involves incubating cells in 2.5% glutaraldehyde (v/v) for 60 min at 37° C., and then washing with media.

Alum was purchased as Alhydrogel™, an aluminum hydroxide gel adjuvant (Brenntak Biosector, Frederikssund, Denmark).

Statistical Analysis—Results of survival versus non-survival following challenge with tetanus toxin were compared between groups using the Chi-square test with two degrees of freedom. Differences were considered significant when $p \leq 0.05$. Results for mean tumor weight were compared between groups with the Wilcoxon rank sum test with significance reached when $p \leq 0.05$.

Example 2

In Vivo Activity of Tumor Cell Vaccine and Cancer Adjuvant

The present example demonstrates the utility of the present invention as an effective cancer vaccine adjuvant in vivo.

Tumor cells were cultured on SIS. Following three days of growth, the SIS with attached cells were fixed with glutaraldehyde. Subcutaneous tumors grown in the flank of Lobund-Wistar rats which had been administered PAIII prostate cancer cells 10 days earlier were surgically resected.

Groups of 5 rats then underwent either no further treatment; treatment with glutaraldehyde-fixed tumor (GFT) cells applied directly on the tumor bed; treatment with glutaraldehyde-fixed (GF) SIS (without cells) applied on the tumor bed; or treatment with glutaraldehyde-fixed SIS (with cells) applied on the tumor bed. Three weeks later, after tumors had re-grown in most rats, tumors were weighed with the following results:

No treatment=mean tumor weight of 11.64 grams
 GFT cells=mean tumor weight of 10.54 grams
 GF SIS=mean tumor weight of 12.31 grams
 GF SIS+GFT cells=mean tumor weight of 4.77 grams The addition of SIS to the GFT cell vaccine resulted in a greater than 50% reduction in mean tumor weight and establishes that SIS is an effective adjuvant for cancer (anti-tumor) vaccination.

Example 3

ECM Supports Cancer Cell Expansion

The present example demonstrates the utility of the invention for providing a method for expanding a cancer cell population on an extracellular matrix material. The present example also demonstrates the utility of the invention for preparing a highly immunogenic population of cells useful in a cancer vaccine preparation. In the case of cancer, it is likely that many key antigens are expressed by connective tissue matrix and involve interactions of neoplastic cells with the extracellular matrix. Cancer cell vaccines grown on an extracellular matrix thus may be prepared according to the present example and used as improved vaccine antigen compositions for vaccination.

1. Fascia Extracellular Matrix Material (FEM)

The present example demonstrates another example of the type of extracellular matrix material that may be used in the practice of the present invention. The present example employs porcine fascia extracellular matrix material (FEM).

Studies were conducted as described herein to examine the ability of tumor cells to grow on FEM. In these studies, it was demonstrated that tumor cells did grow robustly on the FEM material, comparable with that growth supported on the SIS and RCM.

2. Expansion of Prostate Cancer Cells on SIS and RCM in Culture

Previous investigators have demonstrated the ability of pure cell lines to grow on SIS in vitro. For example, Badylak et al (38) showed SIS is capable of supporting cultures of NIH Swiss mouse 3T3 fibroblasts, primary human fibroblasts, keratinocytes, endothelial cells, and an established rat osteosarcoma cell line. The present example demonstrates that an extracellular matrix material preparation as describe herein from SIS supports cancer cell growth. In particular, growth of a prostate cancer cell line and a mixed cell population harvested directly from a subcutaneous tumor (the tumor having been produced by inoculation of rat PAIII cells into a Lobund-Wistar (LW) rat), are shown to grow on the ECM materials under the conditions described here.

Sheets of single-layer SIS and RCM were cut into 2×2 cm sections and placed into Modified Eagle's Medium (MEM). PAIII cells ($1\times10^6$), or cells harvested directly from a PAIII subcutaneous rat tumor ($1\times10^6$), were layered on the SIS and incubated at 37° C. for 72 hours, then fixed in 10% neutral buffered formalin for 24 h, washed in 70% ethanol, placed in paraffin and sectioned at 4-5 µM. Sections were then stained with hematoxylin and eosin stain and examined for cell growth.

Figure 2:
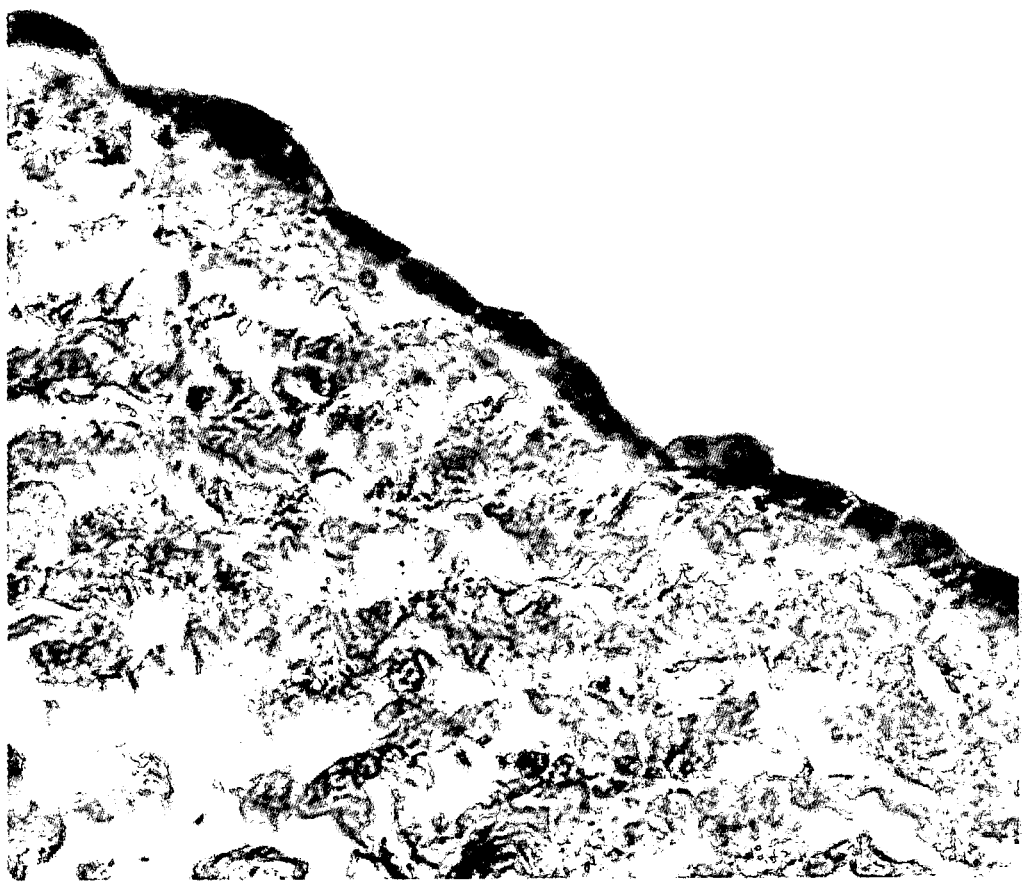
FIG. 2, according to one embodiment of the invention, presents a thin layer of PAIII rat prostate adenocarcinoma cells along the edge of SIS extracellular matrix material. PAIII cells had been co-cultured with SIS for three days. Stained with H & E, 400×.
Figure 3:
FIG. 3, according to one embodiment of the invention, presents a photomicrograph of SIS extracellular matrix material following co-culture for three days with tumor cells obtained directly from a subcutaneous PAIII rat prostate adenocarcinoma tumor. The walls of the remnant blood vessel have been repopulated with cells and nuclei of other cells can be seen within the substance of the SIS. Stained with H & E, 400×.
Figure 4:
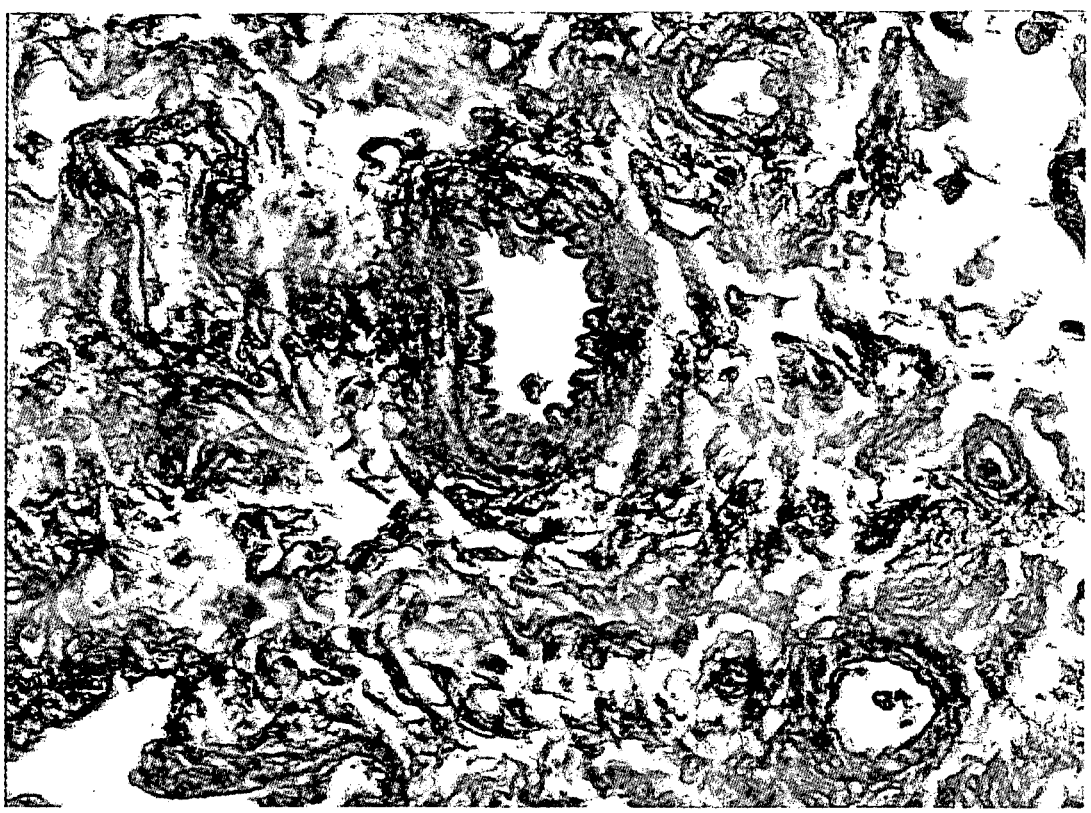
FIG. 4, according to one embodiment of the invention, presents a photomicrograph of SIS extracellular matrix material following incubation for three days in media but with no added cells. There are no nuclei present within the remnant vessel or the substance of the SIS. Stained with H & E, 400×.

Samples which were incubated with pure PAIII cells demonstrated a monolayer of cell growth along the edges of SIS and RCM (FIG. 2). In contrast, culture of cells harvested directly from tumors showed growth of cells along the edges of SIS and RCM. In addition, in the midsubstance; vascular structures were re-populated with cells (FIG. 3) compared to control SIS which had undergone incubation in media but with no cells added (FIG. 4). of Badylak et al (38) showed that rat osteosarcoma cells and endothelial cells grew only on the edge of the ECM, while fibroblasts populated the ECM midsubstance. When co-cultured, keratinocytes and fibroblasts resulted in a distinct spatial orientation of the two cell types and early epidermal structures were formed.

This study demonstrated that prostate cancer cells and mixed cell populations harvested directly from tumors can be grown in culture on three types (FEM, SIS and RCM) of ECM.

Example 4

SIS as a Vaccine Adjuvant to Prevent Regrowth of Tumors Following Surgical Resection In earlier work, the present inventors described the ability of glutaraldehyde-fixed tumor (GFT) cells harvested directly from a PAIII rat tumor to prevent prostate cancer (36). Based upon this, the present example demonstrates that vaccination will inhibit the regrowth of tumors following surgical resection.

The present example demonstrates that an SIS/whole cell vaccine effectively inhibits tumor regrowth following surgical resection and debulking. Studies utilized the Lobund-Wistar (LW) rat prostate cancer model which can be used to induce de novo prostate tumors by chemical induction, or it can be used to grow subcutaneous tumors following implantation of a prostate cancer cell line (PAIII cells).

Using the latter system, PAIII cells were administered subcutaneously to groups of LW rats. Fourteen days after administration of PAIII cells, tumors were surgically debulked and vaccines applied as follows:

Adjuvancy after Growth of Cells on SIS for 3 Days

Vaccine was prepared by allowing tumor cells harvested from a subcutaneous tumor to grow upon SIS in culture for 3 days, after which the material underwent glutaraldehyde fixation (GFT) and washing (GFT vaccine on SIS). Glutaraldehyde fixation involves incubating cells in 2.5% glutaraldehyde (v/v) for 60 min at 37° C., and then washing with media. One group of 5 rats underwent only resection; one group had GFT cell vaccine applied to the tumor bed; one group had SIS applied to the tumor bed; and one group had GFT cell vaccine on SIS applied to the tumor bed. The results in terms of mean tumor re-growth (tumor weight in grams±standard deviation) after 3 weeks are shown in FIG. 5 and were as follows:

Resection only: 11.64±2.14 gm, 4/5 with lung metastases
SIS alone: 13.61±1.4 6 gm, 4/5 with lung metastases
GFT cell vaccine: 9.50±1.27 gm, 3/5 with lung metastases
GFT cell vaccine on SIS: 3.98±0.1.37 gm, 2/5 with lung metastases The tumors in rats vaccinated with the GFT cell vaccine on SIS were significantly smaller ($P \leq 0.01$) than those from rats vaccinated with the GFT cell vaccine alone and the control groups.

Adjuvancy after Growth of Cells on SIS for 28 Days

In a second study, cells were cultured on SIS for 28 days before implantation. The results from this study are shown in FIG. 6 and are as follows:

Resection only: 14.9 gm±2.12, 6/6 with lung metastases
SIS only: 15.6 gm, ±1.82 5/5 with lung metastases
GFT cell vaccine: 11.8 gm±1.46, 4/5 with metastases
GFT vaccine on SIS: 6.01 gm±1.17, 2/5 with lung metastases Thus, the result is repeatable and demonstrates that the GFT vaccine on SIS also inhibited metastasis from the primary tumor to the lungs. These data were not quite significant (probability of 0.053) due to the small group size.

These data support the idea that efficacy of cancer vaccines is improved by growth of vaccine cells on, or incorporation into, extracellular matrices such as SIS.

Example 5

SIS Gel Acts as an Adjuvant for a Vaccine to Prevent Cancer

Because implantation of vaccines incorporated onto solid SIS matrix would require incision of tissue, it may not be practical for all applications. Thus, the present example demonstrates the utility of the invention to provide a vaccine against cancer in a gel form using an extracellular matrix material, such as SIS, and the use of same as a vaccine adjuvant.

SIS gel is supplied by Cook Biotech, Inc. (West Lafayette, Ind.) and is produced from SIS material via an acid digestion and purification process.

SIS gel was diluted 1:10 with sterile saline. Harvested, glutaraldehyde-fixed cells from PATH tumors were mixed into the SIS gel dilution such that each 0.25 ml dose of SIS gel contained $5 \times 10^6$ GFT cells.

Groups of ten (10) male LW rats were administered subcutaneously the following:

0.25 ml of SIS gel;
0.25 ml of SIS gel+GFT cells;
0.25 ml of sterile saline containing $5 \times 10^6$ GFT cells; or
0.25 ml saline.

Rats were vaccinated 3 times, 7 days apart. Seven days after the last vaccination, all rats were challenged subcutaneously with $1 \times 10^6$ PAIII cells.

Figure 7:
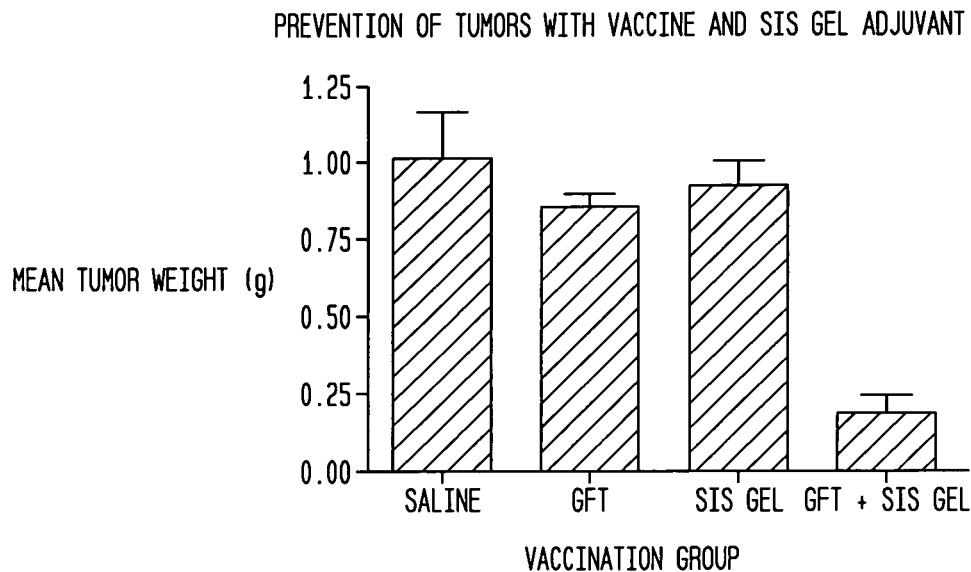
FIG. 7, according to one embodiment of the invention, demonstrates the adjuvancy of SIS gel for the GFT cell vaccine in preventing tumor growth. Rats were vaccinated three times, seven days apart, with either SIS gel; SIS gel with GFT cells; GFT cells; or saline prior to subcutaneous challenge with PAIII cells. Bars represent mean group tumor weights (±standard deviation). A significant (P≤0.01) reduction in mean tumor weight was found in rats vaccinated with the GFT cell vaccine in SIS gel compared to all other treatment groups.

Three weeks after challenge with PAIII cells, rats were euthanized and tumors weighed. The results are shown as mean tumor weights (±standard deviation) in FIG. 7 and are as follows:

Saline=1.02 g (±0.37), 5/6 rats with metastases to the lungs
GFT cell vaccine=0.86 g (±0.11), 6/10 rats with metastases to the lungs
GFT cell vaccine in SIS gel=0.19 (±0.14), 1/10 rats with metastases to the lungs As can be seen in FIG. 7, treatment with the GFT cells alone resulted in a tumor size of approximately 0.86 g.+/−0.11 g., while treatment with GFT cells in the extracellular matrix material (SIS) in a gel form resulted in a tumor growth of approximately 0.19 g.+/−0.14 g., about one-fourth the size. Hence, the addition of the extracellular matrix gel (SIS) in a 1:10 dilution significantly adjuvinated the tumor growth inhibiting activity of the GFT cell preparation (fixed prostate cell vaccine antigen) about 4-fold to about 5-fold. Thus, it is demonstrated here that the addition of an extracellular matrix material to a cell-based cancer vaccine will significantly adjuvinate a tumor cell preparation used as a vaccine, by 2-fold or greater.

Example 6

SIS Gel Acts as a Vaccine Adjuvant for the Treatment of Cancer

The present example demonstrates the utility of the present invention for providing an enhancement of immunity effective both as a preventive measure and as a therapeutic measure.

In the present example, groups of six rats were challenged subcutaneously with $1\times10^6$ PAIII cells to create tumors. Animals were vaccinated 3 times, 7 days apart; rats underwent surgical resection of tumors ten days after challenge, three days after the first vaccination. An additional group was included in which animals were vaccinated by subcutaneous implantation of GFT cell vaccine on a sheet of SIS. Animals were euthanized 21 days after tumor resection and tumors weighed.

Figure 8:
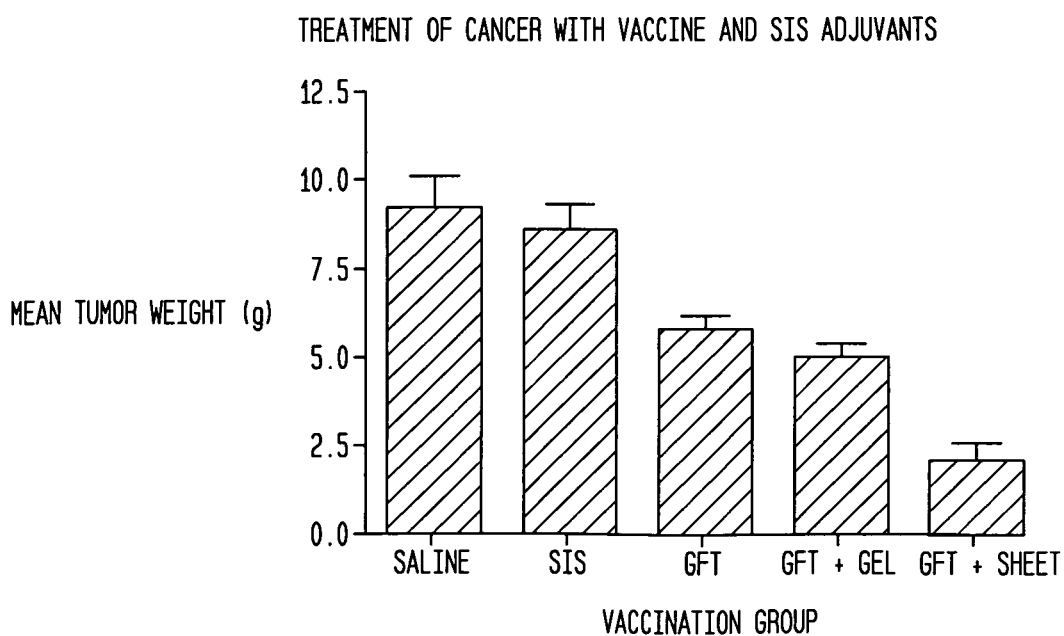
FIG. 8, according to one embodiment of the invention, demonstrates the adjuvancy of SIS gel and sheet SIS for the GFT cell vaccine in treatment of PAIII prostate adenocarcinoma tumors following resection. Tumor-bearing rats were vaccinated three times, 7 days apart with either saline; SIS with no added cells; GFT cell vaccine; GFT cell vaccine in SIS gel; or GFT cell vaccine on SIS. Three days after the first vaccination, tumors were surgically resected; 21 days after resection, animals were euthanized and tumors weighed. Bars represent mean group tumor weights±standard deviation. Mean tumor weights for rats vaccinated with the GFT cell vaccine alone or in gel SIS were significantly (P≤0.05) less than rats vaccinated with saline or SIS with no added cells. Mean tumor weight for rats vaccinated with the GFT cell vaccine on a sheet of SIS was significantly (P≤0.01) less than all other treatment groups.

The results from this study are shown in FIG. 8 and are summarized as:

| Treatment Group | Mean tumor weight (g) ± SD, Lung Metastases |
|---|---|
| Saline Controls | 9.2 ± 2.2 g, 6/6 with metastases |
| SIS alone | 8.6 ± 1.8 g, 6/6 with metastases |
| GFT cell vaccine | 5.8 ± 0.9 g, 4/6 with metastases |
| GFT cell vaccine in SIS gel | 5.0 ± 0.8 g, 3/6 with metastases |
| GFT cell vaccine on SIS sheet | 2.1 ± 1.1 g, 3/6 with metastases |

Figure 9:
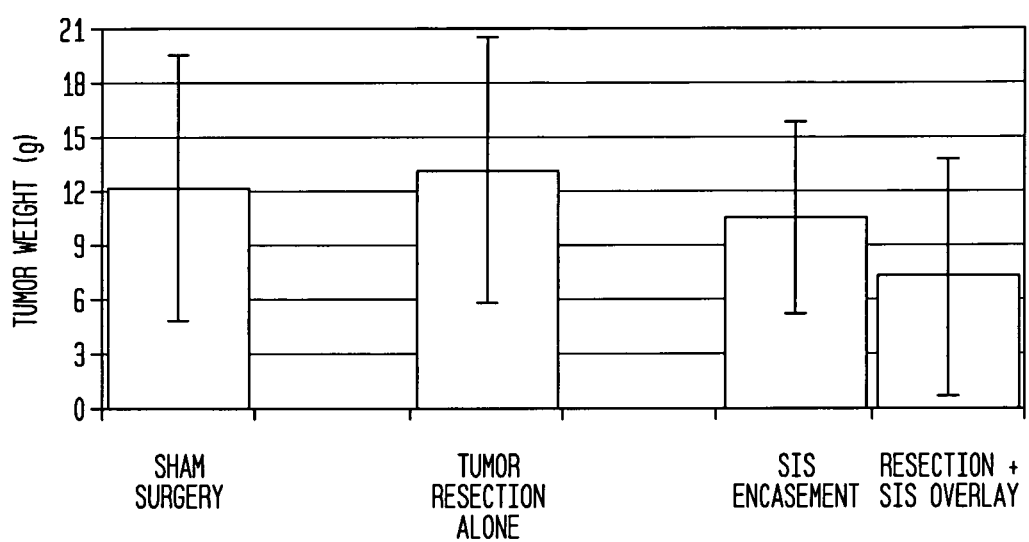
FIG. 9, according to one embodiment of the invention, demonstrates the effect of SIS implantation on tumor recurrence. PAIII tumors recurred in all animals within 3 weeks of resection. Size of explanted tumors in the sham surgery group demonstrates a slower growth rate in tumors that reach a critical size. *SIS overlay limited the size of the tumors that recurred (P=0.0009, versus tumor resection alone). Data are presented as mean±1 SD.

These studies demonstrate that SIS gel has vaccine adjuvant activity and can enhance protective immunity to cancer both before cancer cell challenge and as an adjunct to surgical resection. This means that SIS gel enhances immunity effective as a preventative measure (i.e., as a vaccine), and as a therapeutic measure (FIG. 9).

Example 7

Safety of GFT Vaccine and ECM Adjuvants

The present example demonstrates the utility of the present invention as a clinically acceptable preparation for animal, including human, treatment. In particular, the present example demonstrates that the preparations do not induce tissue damage, and does not result in autoimmune disease.

Both the GFT cell vaccine and SIS are safe to use in vivo. The present example demonstrates that repeated administration of the GFT cell vaccine failed to induce histopathologic or clinical disease in rats. In addition, the present example demonstrates that SIS did not promote tumor growth in vivo, and further demonstrated inherent inhibition of tumor growth in the LW rat tumor model. Furthermore, SIS is already approved by the U.S. Food and Drug Administration as a medical device for a variety of applications.

The present study demonstrates that repeated vaccination with the present preparations does not result in histological evidence of autoimmune disease.

Groups of 10 three-month-old LW rats were each immunized and boosted monthly for 12 months with either MEM or GFT cells. Freund's complete adjuvant was used for the initial vaccination, and Freund's incomplete adjuvant was used for booster vaccinations. Tissues were then harvested at 15 months of age, fixed in 10% neutral buffered formalin, sectioned at 3-4 nm and stained with hematoxylin and eosin. All rats were clinically normal for the duration of the study. Kidney, heart, brain, liver, testis, prostate/seminal vesicle, and spleen were examined and all found to be histologically normal.

These results demonstrate that repeated immunization with the GFT cell vaccines does not induce tissue damage suggestive of autoimmunity.

Example 8

SIS Does Not Promote Growth of Tumor Tissue When Placed In Vivo

The present example demonstrates the utility of the extracellular matrix material preparations as providing an anti-tumor activity with a tumor/cancer cell preparation. The present example also demonstrates that the present preparations do not themselves induce tumor and/or cancer growth.

Because cancer cells showed an ability to grow on SIS and RCM in vitro, it is important to determine if an ECM, such as SIS, would promote the growth of residual tumor cells if placed on the bed of a resected tumor in vivo.

To evaluate this, groups of 25 male LW rats, age 3 months, underwent induction of subcutaneous PAIII tumors as described above. Animals were then assigned to one of four different treatment groups:
sham surgery control;
physical encasement of the tumor with SIS (tumor was not dissected from the underlying vascular bed);
complete tumor resection (all grossly visible tumor was removed); or
complete tumor resection followed by overlying the resected tumor bed with SIS (approximately 3×3 cm).

Three weeks later, rats were euthanized and the tumors weighed. The results (FIG. 9) show that SIS did not promote growth of PAIII tumors compared to sham surgery or resection alone. Overlying of the resected tumor bed with SIS led to a significant ($P\leq0.0009$) decrease in tumor size versus resection alone (39).

In culture, cancer cell lines and cancer tissue from harvested tumor material both grow rapidly on SIS and RCM. When inactivated by glutaraldehyde fixation, cancer cells and tissue grown on SIS prevent regrowth of tumors following surgical resection. This effect is observed when cells are grown on SIS, and also when glutaraldehyde-fixed tumor cells are mixed into a gel form of SIS. Furthermore, SIS gel is shown to act as a vaccine adjuvant to prevent the development of cancer; that is, to stimulate protective immunity to challenge with live PAIII cells.

ECM materials, as demonstrated by SIS and RCM, both initiate a robust inflammatory response when implanted in vivo. While not intending to be limited to any particular theory or mechanism of action, it is believed that any antigenic moieties carried along, whether adhered to the ECM or present in a gel or a particulate suspension, will be processed by the immune system, thus possibly accounting for at least one theory by which the ECM may act as a vaccine adjuvant.

It is known that SIS contains a variety of bioactive species, including TGF-$\beta$ (41). While TGF-$\beta$ can act as a tumor promoter in later stages of tumor progression, it functions as a tumor suppressor in early tumorigenesis (42). Thus, administered at the proper time, such as following resection, the utility discovered herein for SIS to inhibit tumor growth may be utilized.

Example 9

Proposed Regimen for Clinical Application, Sheet SIS

The present example is provided to demonstrate the utility of the present vaccines in SIS for providing a treatment for cancer and/or to reduce/inhibit tumor growth by use of SIS in a sheet-like preparation.

Approach without Surgical Tumor Resection:
While vaccines based on an extracellular matrix have not been described, use of a prostate cancer vaccine comprised of inactivated allogeneic whole prostate cancer cell lines has been described (Michael, et al)(2005)(47). In that study, monthly intradermal injections for 12 months of $8\times10^6$ inactivated whole cells were administered, the first two in a standard adjuvant, alum, to patients with hormone-resistant prostate cancer. The adjuvant used in the first two doses administered was bacilli Calmette-Guerin. The first three doses were given at weekly intervals, and once a month thereafter. This approach led to statistically significant declines in PSA (prostate-specific antigen) velocity with no evidence of toxicity. Further, median time to a defined point of disease progression was increased to 58 weeks from approximately 28 weeks.

A whole cell prostate cancer vaccine together with a preparation of the extracellular matrix adjuvant (diluted 1×10 from a commercial preparation, such as that commercially available from a vendor such as Cook Biotech, Inc.) would be used according to the present invention under a clinical regimen wherein the vaccine would be administered intradermally or subcutaneously on a monthly basis for approximately 12 months.

Vaccine preparations which can be easily injected, such as those including SIS gel or a particulate form of SIS as adjuvant would be administered by percutaneous injection.

A vaccine preparation which includes vaccine fixed on a sheet of SIS would be administered either percutaneously by trochar into the subcutaneous space or, in other embodiments, by implantation via a small incision made into the skin.

Approach with Surgical Resection:

Few studies have looked at the utility of vaccination in conjunction with surgical resection of a tumor. Pilla et at (2006)(49) administered subcutaneously tumor-derived heat shock protein gp96-peptide complex vaccine to advanced stage melanoma patients for up to four treatments, two weeks apart, following surgical resection. That approach resulted in stabilization of disease in 11/18 patients post-surgically. Berd et al (1997)(50) administered an inactivated autologous whole cell vaccine on a weekly or monthly schedule to melanoma patients with clinically evident lymph node metastases; this approach resulted in survival rates superior to those resulting from surgery alone.

While no studies have looked at the utility of vaccination directly on the tumor bed of a resected prostate tumor, nor the utility of a vaccine incorporated onto a solid-phase adjuvant such as an extracellular matrix, the present examples demonstrate specific clinical use applications of the vaccine. Some embodiments of the present invention will provide the vaccine incorporated onto a sheet of extracellular matrix, and will be applied as a sheet directly onto the resected tumor bed at the time of surgery; or administered intradermally or subcutaneously at a site beyond the tumor bed on a monthly basis. A similar approach used with a different vaccine is described by Berd et al (1997) (50) using a whole cell vaccine for the treatment of melanoma.

In other embodiments, a combination approach may be used in which vaccination is made directly onto the tumor bed, and is applied at the time of resection followed by booster vaccinations given intradermally or subcutaneously.

The sheet vaccine would be administered percutaneously by trochar into the subcutaneous space or, possibly, by implantation via a small incision made into the skin. Vaccine preparations which can be easily injected, such as those including SIS gel or a particulate form of SIS as adjuvant, would be administered by direct application of the material onto the tumor bed and/or intramdermally or subcutaneously by injection. Bell et al. (2005) (65).

Example 9

Dermal Application of Vaccines

The present example demonstrates the utility of the invention for providing a dermally-applicable formulation of the tissue based adjuvant cancer preparations.

While transdermal vaccination has been used for diseases associated with infectious pathogens (Kenney, 2004(59); Skountzou, 2006 (60); Glenn, 2006 (61), very few attempts have been made to apply this route of administration to cancer vaccines. Transcutaneous immunization was used in mice by administering imiquiod, a cytotoxic T lymphocyte (CTL) activator, in an ointment applied to shaved skin (Rechsteiner, 2005 (62)); this approach stimulated CTL activity in general and not against any specific cancer antigen. Other investigators described an anti-tumor vaccine by delivery to mice of human carcinoembryonic antigen gene in an adenovirus vector via a thin film of vector placed onto the shaved skin and beneath a patch (Huang, 2005 (63)). This approach resulted in immunologic resistance to challenge with murine mammary adenocarcinoma cells.

According to use in the present invention, the cancer antigen of interest, such as a glutaraldyhyde fixed preparation of prostate cells, may be prepared in a formulation together with a gel form of the extracellular matrix material, SIS. In this formulation, the preparation may be applied to an area to provide the anti-tumor effect.

Further features of embodiments of the present invention may be found in U.S. Provisional Patent Application No. 60/730,379 entitled "Use of Extracellular Matrix Materials as a Vaccine Carrier and Adjuvant", filed Oct. 27, 2005, and to U.S. Ser. No. 11/209,766, entitled "Tissue Vaccines and Uses Thereof", filed Aug. 24, 2005. The entire disclosure and contents of the above applications are hereby incorporated by reference herein.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

BIBLIOGRAPHY

The references listed below as well as all references cited in the specification are incorporated herein by reference to the extent that they supplement, explain, provide a background for or teach methodology, techniques and/or compositions employed herein.

1. Edwards B K, et al., (2005); *J Natl Cancer Inst,* 97(19): 1407-27.
2. Greenlee R T, et al., (2001), "Cancer Statistics", *CA Cancer J Clin,* (2001); 51:15-36.
3. Simons J W, Sacks N., (2006), *Urol. Oncol.,* 24:419-424.
4. Fukino K, et al., (2004), *Cancer Res.,* 64(20):7231-6.
5. Bissell M J, et al., (1987), *J. Cell Sci. Suppl.,* 8(3):327-43.
6. Matrisian L M, et al., (2001), *Cancer Res.,* 61(9):3844-6.
7. Shekhar M P, et al., (2001), *Cancer Res.,* 61(4):1320-6.
8. Tatenhorst L, et al., (2005), *Brain Pathol,* 15(1):46-54.
9. Moschella F, et al., (2003), *Oncol Res.,* 14(3):133-45.
10. Brewer J. M., *Immunol Lett.,* (2006); 102(1):10-5.
11. Lindblad, E B, (2004), *Immunol Cell Biol.,* 82(5):497-505.
12. Barr, T A, et. al., (2006), *Vaccine,* 24(17):3399-407.
13. Hodge, J. W., *Front Biosci,* (2006); 11:788-803.
14. Knoll L. D., (2001), *Urology,* 57:753-757.
15. Knoll L. D., (2002), *Urology,* 59:758-761.
16. Mantovani F, et al., (2003), *Eur Urol.,* 44:600-602.
17. O'Conner R C, et al., (2001), *J Urology,* 165:1995.
18. O'Connor R C, et al., (2002), *Urology,* 60:697x-697xii.

19. O'Connor R C, Harding J N, Steinberg G D., *Urology.* (2002); 60:906-909.
20. Paradiso M, et. al., (2003) *Arch Ital Urol. Androl.,* 75:116-118.
21. Weiser A C, et al., (2003), *J. Urol,* 170:1593-1595.
22. Oasis, Benbow M., (2001), *Br. J. Nurs.,* 10:1489-1492.
23. Brown-Etris M, et al., (2002), *Wounds,* 14:150-166.
24. Schultz D J, et al., (2002), *J. Am. Coll. Surg.,* 194:541-543.
25. Suckow M A, et al., (1999), *Journal of Investigative Surgery,* 12:277-287.
26. Badylak, S. F., *Small Intestinal Submucosa (SIS): A Biomaterial Conducive to Smart Tissue Remodeling, Tissue Engineering: Current Perspectives,* Bell E (ed). Burkhauser Publishers, Cambridge, Mass., (1993), pp. 179-189.
27. Badylak, S. F., (2002), "The Extracellular Matrix as a Scaffold for Tissue Reconstruction", *Seminars in Cellular and Developmental Biology,* 13:377-383.
28. Suckow M A, et al., (2005), *J. Wound Care,* 14:137-140.
29. Suckow M A, et al., (In Press), *J. Mater Sci. Mater. Med.*
30. Lantz, G. C., et al., (1993), *J. Invest. Surg.,* 6:297.
31. Badylak, S. F., et al., (1989), *J. Surg. Res.,* 47:74.
32. Lantz, G. C., et al., (1990), *J. Invest. Surg.,* 3:217.
33. Hodde, J. P., and Hiles, M. C., (2002), *Biotechnol. Bioeng,* 79:211.
34. Pollard M, Suckow M. A., (2005), *Experimental Biology and Medicine,* 230:520-526.
35. Suckow M A, et al., (2005), *Cancer Immunology and Immunotherapy,* 54:571-576.
36. Pollard M, Luckert P. H., (1975), *J. Natl. Cancer Inst.,* 54:643-49.
37. Badylak S F, et al., (1998), *Journal of Biomaterials Sciences Polymer Edition,* 9:863-878.
38. Hodde, J P, et al., (2004), *J. Surg. Res.,* 120: 189-194.
39. Culora G A, (1996), *J. Clin. Pathol,* 49:844-847.
40. McDevitt C A, et al., (2003), *J. Biomed. Mater. Res.,* 67A:637-646.
41. Bello-DeOcampo D, Tindall D. J., (2003), *Curr. Drug Targets,* 4:197-210.
42. Gu, Y., and Dai, K., Zhonghua Yi Xue Za Zhi. (2002); 82:1279.
43. Voytik-Harbin S. L., et al., (1998), *Tissue Eng.,* 4:157-174.
44. U.S. Pat. No. 7,015,205 to Wallack, et al. (2006).
45. U.S. Pat. No. 6,548,066 to Michaeli, et al. (2003)
46. U.S. Pat. No. 7,090,853 to Kapp, et al. (2006)
47. Michael A., et al., (2005), *Clin Cancer Res.,* 11:4469-4478.
48. Pilla L, et al., (2006), *Cancer Immunol Immunother.,* 55:958-968.
49. Berd D, et al., (1997), *J. Clin Oncol.,* (1997); 15:2359-2370.
50. Petrovsky N., (2006), *Vaccine,* 24 Suppl. 2:S2-26-9.
51. Bendandi, M. et al., (2006), *Leuk. Lymphoma,* 47:29-37.
52. Redfern C. H., et al., (2006), *J Clin Oncol.,* 24:3107-12.
53. Totterman T H, et al., (2005), *BJU Int,* 96:728-735.
54. Mosolits S, et al., (2005), *Expert Rev. Vaccines,* 4:329-350.
55. He X, et al., (2005), *Vaccine,* 23:1966-1972.
56. Wei Y, Sticca R. P., et al., (2006), *Int. J. Oncol.,* 28:585-593.
57. Rousseau R F, et al., (2006), *Blood,* 107:1332-1341.
58. Simons J W, Sacks N., (2006), *Urol. Oncol.,* 24:419-424.
59. Kenney R T, et al., (2004), *J. Infect. Dis.,* 190:774-782.
60. Skountzou I, et al., (2006), *Vaccine,* 24:6110-6119.
61. Glenn G M, Kenney R. T., (2006), *Curr. Topics Microbiol. Immunol.,* 304:247-268.
62. Rechsteiner G, et al., (2005), *J. Immunol.,* 174:2476-2480.
63. Huang C. M, et al., (2005), *Proteomics,* 5:1013-1023.
64. Bell et al., (2005), *Clin. Cancer Res.,* 11:4469-4478.

What is claimed is:

1. A composition comprising a tumor tissue cell suspension comprising replication incompetent tumor cells, and an adjuvant comprising extracellular matrix from a non-tumor source.

2. A composition comprising a prostate tumor tissue cell suspension comprising replication incompetent human prostate tumor cells, and an adjuvant comprising extracellular matrix from a non-tumor source.

3. The composition of claim 1 prepared by a method comprising:
  obtaining an adjuvant comprising extracellular matrix from a non-tumor source, said extracellular matrix being capable of enhancing the immunogenicity of a tumor tissue cell suspension; and
  combining said adjuvant with a tumor tissue cell suspension of replication incompetent tumor cells.

4. The composition of claim 1 or 2 further defined as a pharmaceutical preparation.

5. The composition of claim 1 wherein the replication incompetent tumor cells are replication incompetent human tumor cells.

6. An implantable preparation comprising the composition of claim 1 or 2.

7. The implantable preparation of claim 6 wherein the extracellular matrix is in the form of a sheet, gel or particle.

8. The implantable preparation of claim 6 wherein the extracellular matrix is a gel.

9. The composition of claim 2 wherein the composition is essentially free of alum.

10. The composition of claim 2 wherein the prostate tumor cells are rendered replication incompetent by glutaraldehyde treatment.

11. The composition of claim 1 wherein the extracellular matrix is in a sheet, particle or gel form.

12. The composition of claim 1 wherein the source of the extracellular matrix is small intestinal submucosa.

13. A method for inhibiting growth of a tumor in an animal comprising administering to an animal having a tumor the composition of claim 1, wherein the tumor tissue cell suspension comprises tumor cells obtained from the animal to be treated.

14. A composition suitable for treating cancer comprising a tumor tissue cell suspension comprising replication incompetent tumor cells, and
  an adjuvant comprising extracellular matrix from a non-tumor source.

15. A prostate cancer treatment composition comprising a human prostate tumor tissue cell suspension comprising replication incompetent prostate tumor cells, and
  an adjuvant comprising extracellular matrix from a non-tumor source.

16. A method for stimulating an immune response in an animal in need thereof against a cancer tissue comprising:
  administering to said animal a composition comprising a tumor tissue cell suspension of replication incompetent tumor cells, and an adjuvant comprising extracellular matrix from a non-tumor source.

17. The method of claim 16 wherein the tumor tissue cell suspension is a prostate tumor tissue cell suspension.

18. A composition comprising a replication incompetent tumor tissue cell suspension and extracellular matrix, wherein said extracellular matrix is from a non-tumor source and in the form of a gel.

19. A method for inhibiting tumor growth in an animal in need thereof comprising administering the composition of claim 18.

* * * * *